(12) United States Patent
Sundararajan et al.

(10) Patent No.: US 9,096,953 B2
(45) Date of Patent: Aug. 4, 2015

(54) METHOD FOR HIGH THROUGHPUT, HIGH VOLUME MANUFACTURING OF BIOMOLECULE MICRO ARRAYS

(75) Inventors: Narayan Sundararajan, San Francisco, CA (US); John J. Rajasekaran, Los Altos, CA (US); Guangyu Xu, Milpitas, CA (US); Gunjan Tiwari, Sunnyvale, CA (US); Edelmira Cabezas, Sunnyvale, CA (US)

(73) Assignee: INTEL CORPORATION, Santa Clara, CA (US)

( * ) Notice: Subject to any disclaimer, the term of this patent is extended or adjusted under 35 U.S.C. 154(b) by 2356 days.

(21) Appl. No.: 11/529,573

(22) Filed: Sep. 29, 2006

(65) Prior Publication Data

US 2010/0240555 A1 Sep. 23, 2010

(51) Int. Cl.
| | | |
|---|---|---|
| B82Y 30/00 | (2011.01) | |
| C40B 50/18 | (2006.01) | |
| B01J 19/00 | (2006.01) | |
| B82Y 5/00 | (2011.01) | |
| C40B 40/06 | (2006.01) | |

(52) U.S. Cl.
CPC .............. *C40B 50/18* (2013.01); *B01J 19/0046* (2013.01); *B82Y 5/00* (2013.01); *B82Y 30/00* (2013.01); *B01J 2219/00432* (2013.01); *B01J 2219/00495* (2013.01); *B01J 2219/00527* (2013.01); *B01J 2219/00612* (2013.01); *B01J 2219/00617* (2013.01); *B01J 2219/00637* (2013.01); *B01J 2219/00659* (2013.01); *B01J 2219/00711* (2013.01); *B01J 2219/00725* (2013.01); *C40B 40/06* (2013.01)

(58) Field of Classification Search
None
See application file for complete search history.

(56) References Cited

U.S. PATENT DOCUMENTS

| | | | |
|---|---|---|---|
| 4,863,827 A | | 9/1989 | Jain et al. |
| 5,143,854 A | * | 9/1992 | Pirrung et al. ............... 436/518 |
| 5,405,783 A | | 4/1995 | Pirrung et al. |
| 6,083,697 A | * | 7/2000 | Beecher et al. ................ 506/40 |
| 6,121,048 A | | 9/2000 | Zaffaroni et al. |
| 6,159,681 A | | 12/2000 | Zebala |
| 6,239,273 B1 | | 5/2001 | Pease et al. |
| 6,379,895 B1 | | 4/2002 | Fodor et al. |
| 6,406,844 B1 | | 6/2002 | Pirrung et al. |
| 6,410,213 B1 | * | 6/2002 | Raguin et al. ................ 430/321 |
| 6,416,952 B1 | | 7/2002 | Pirrung et al. |
| 6,426,184 B1 | | 7/2002 | Gao et al. |
| 6,506,558 B1 | | 1/2003 | Fodor et al. |
| 6,515,039 B1 | | 2/2003 | Ulbricht et al. |
| 6,566,495 B1 | | 5/2003 | Fodor et al. |
| 6,589,726 B1 | | 7/2003 | Butler et al. |
| 6,630,308 B2 | | 10/2003 | Stryer et al. |
| 6,770,436 B1 | | 8/2004 | Beecher et al. |
| 6,819,843 B1 | | 11/2004 | Braun et al. |
| 6,919,211 B1 | | 7/2005 | Fodor et al. |
| 7,247,337 B1 | * | 7/2007 | Leproust et al. ............... 427/2.1 |
| 2006/0061754 A1 | | 3/2006 | Turner et al. |
| 2006/0237430 A1 | * | 10/2006 | Quach et al. ................ 219/444.1 |
| 2007/0122842 A1 | | 5/2007 | Rajasekaran et al. |
| 2007/0154946 A1 | | 7/2007 | Rajasekaran et al. |
| 2008/0161202 A1 | | 7/2008 | Cabezas et al. |

FOREIGN PATENT DOCUMENTS

KR          100379411          3/2003

OTHER PUBLICATIONS

Linda Geppert (Associate Editor), 'Semiconductor Lithography for the next millennium', IEEE Spectrum, Apr. 1996—See a stepper-scanner lithography system performing illumination of UV light at pp. 34-36.
Jean Philippe Pellois, et al., "Individually Addressable Parallel Peptide Synthesis on Microchips", Nature biotechnology, vol. 20, Sep. 2002 (pp. 922-926).
C. Grant Willson, et al., "Approaches to the Design of Radiation-Sensitive Polymeric Imaging Systems with Improved Sensitivity and Resolution", J. Electrochem. Soc.: Solid-State Science and Technology, vol. 133, No. 1, Jan. 1986 (pp. 181-187).
Masamitsu Shirai, et al., "Photoacid and Photobase Generations: Chemistry and Applications to Polymeric Materials", Prog. Polym. Sci., vol. 21, 1996 (pp. 1-45).
James F. Cameron, et al., "Photogeneration of Organic Bases from *o*-Nitrobenzyl-Derived Carbamates", J. Am. Chem. Soc. 1991, vol. 113 (pp. 4303-4313).
James F. Cameron, et al., "Base Catalysis in Imaging Materials. 1. Design and Synthesis of Novel Light-Sensitive Urethanes as Photoprecursors of Amines", J. Org. Chem. 1990, vol. 55 (pp. 5919-5922).
Jean M. J. Fréchet, "The Photogeneration of Acid and Base Within Polymer Coatings: Approaches to Polymer Curing and Imaging", Pure & Appl. Chem., vol. 64, No. 9, 1992 (pp. 1239-1248).
U.S. Appl. No. 11/585,413, filed Oct. 23, 2006 entitled "Solid-Phase Mediated Synthesis of Molecular Microarrays", Inventor(s): Narayan Sundararajan, et al.

(Continued)

*Primary Examiner* — Christopher M Gross
(74) *Attorney, Agent, or Firm* — Pillsbury Winthrop Shaw Pittman LLP

(57) ABSTRACT

The embodiments of the invention relate to a system and method for making a biomolecule microarray comprising a spacer attachment module adapted to attach a linker to a substrate surface of the biomolecule microarray, a coupling module adapted to couple a molecule to the linker, the molecule being capable of forming a peptide bond and containing a protecting group that prevents the formation of the peptide bond, and a deprotection module adapted to create deprotection of the protecting group with a radiation exposure of about 1-50 mJ/cm².

22 Claims, 11 Drawing Sheets

(56) References Cited

OTHER PUBLICATIONS

U.S. Appl. No. 11/641,244, filed Dec. 19, 2006 entitled "Molecular Microarrays and Helical Peptides", Inventor: Edelmira Cabezas.

U.S. Appl. No. 11/647,579, filed Dec. 29, 2006 entitled "Fluorogenic Peptide Substrate Arrays for Highly Multiplexed, Real-Time Monitoring of Kinase Activities", Inventor(s): Gunjan Tiwari, et al.

U.S. Appl. No. 11/529,554, filed Sep. 29, 2006 entitled Aptamer biochip for Multiplexed Detection of Biomolecules, Inventor(s): David J. Lui, et al.

U.S. Appl. No. 11/646,600, filed Dec. 28, 2006 entitled "Quality Control Methods for the Manufacture of Polymer Arrays", Inventor(s): Gordon Holt, et al.

U.S. Appl. No. 11/647,580, filed Dec. 29, 2006 entitled "Novel Strategy for Selective Regulation of Background Surface Property in Microarray Fabrication and Method to Eliminate Self Quencing in Micro Arrays", Inventor(s): Edelmira Cabezas, et al.

* cited by examiner (I)

(II)

(III)

(IV)

(V)

(VI)

(VII)

(VIII)  (IX)

(X)  (XI)

(XII)

(XIII)

METHOD FOR HIGH THROUGHPUT, HIGH VOLUME MANUFACTURING OF BIOMOLECULE MICRO ARRAYS

RELATED APPLICATIONS

This application is related to U.S. Ser. No. 11/291,296, filed Nov. 30, 2005, and Ser. No. 11/395,899, filed Mar. 30, 2006 the disclosures of which are incorporated herein by reference.

FIELD OF INVENTION

The embodiments of the invention relate to a method of high volume manufacturing (HVM) of biomolecule microarray and to HVM semiconductor manufacturing tool sets and links for biomolecule microarray synthesis. The invention transcends several scientific disciplines such as, biochemistry, physics, microelectronics, immunology, molecular biology, and medical diagnostics.

BACKGROUND

An increasing amount of biological assays, such as immunoassays and gene sequencing, are being carried out on micro arrays, such as DNA micro arrays or protein micro arrays. Micro arrays are also emerging as popular analytical tools for genomics and proteomics research. A microarray is a collection of microscopic spots containing probes, typically biological molecules such as DNA or protein spots attached to a solid planar surface, such as glass, plastic or silicon chip in a specific pattern and is used for analyzing biological interactions. Multiple probes can be assembled on a single substrate by techniques well know to one skilled in the art. A probe could bind to an analyte or group or analytes by hybridization or affinity binding. Examples of uses of such an array include, but are not limited to, investigations to determine which genes are active in cancer, investigations to determine which gene differences make a patient have a bad reaction to a drug treatment, investigations for infectious disease, investigations to determine presence of genetic mutation in a patient.

The in situ synthesis of micro arrays using solid-state chemistry and photolithography by a method called light-directed spatially addressable parallel chemical synthesis allows many micron-sized spots, each containing a unique protein/peptide sequence, to be simultaneously synthesized on a glass surface. This method uses a photolabile protection group to mask the N-terminus of an amino acid, and the glass surface during the peptide synthesis. Each deprotection and coupling cycle of the peptide synthesis is controlled by a set of photo masks with defined configurations that allow for the selection deprotection of the N-terminal amino group of the growing peptide chain, followed by selective coupling of different amino acids onto different peptides.

While DNA arrays have been quicker to develop and have emerged as a very powerful tool in genomics, there still exist bottlenecks in terms of the throughput of array synthesis as serial processes that involve manual intervention are used even when they are synthesized using photolithographic techniques. Proteins/peptides are fundamentally different from nucleic acids and the synthesis of protein/peptide arrays is much more complex than DNA arrays. The major impediment of using photolithography to generate high-density peptide arrays arises from the relatively high technical complexity need for peptide array construction with 20 amino acid building blocks, 20 photolabile protecting group containing amino acid derivatives and 20 different masks needed for each monomer elongation cycle. Therefore, the development of protein/peptide arrays has been slower and is still in its infancy. Whereas in the case of DNA arrays, only 4 masks are needed for each coupling cycle. Furthermore, peptide synthesis in general is much less efficient than the oligonucleotide synthesis, making it extremely difficult to generate high-quality peptide/protein arrays.

In generally, depending on the method by which the microarray is created, it can be (a) in situ photolithographic array, (b) in situ SPOT synthesized array, and (c) contact printing (also called spotting) array.

The chemistry of the in situ photolithographic array uses light directed parallel chemical synthesis and solid-state chemistry. This approach is limited largely due to the inefficient photochemical reaction needed throughout the whole synthesis. As a result, only short peptides (or peptide analogs, e.g., peptoids) can be sufficiently synthesized by the in situ photolithographic synthesis approach.

The SPOT-synthesis approach is also by in situ synthesis, but it does not use photochemical reactions for deprotection of the N-terminal amino group of the growing peptide chain. The SPOT-synthesis comprises the dispensing of a small volume of solutions containing Fmoc-amino acids and other coupling reagents to a designated stop on a membrane. Subsequently, deprotection and coupling steps synthesize the biomolecule on the substrate to form protein/peptide array.

The contact printing array method makes use of an automatic spotter to spot nanoliter droplets of pre-synthesized peptide/protein solutions onto a suitably derivatized solid surface, e.g., glass surface. By this approach, each peptide/protein is synthesized only once in a bulk quantity, and multiple spots containing the peptide/protein are created by printing using a spotter.

The more preferred methods for making protein/peptide arrays are contact printing and SPOT-synthesis. The SPOT-synthesis and contact printing methods permit rapid and highly parallel synthesis of huge numbers of proteins/peptides and proteins/peptide mixtures (pools) including a large variety of unnatural building blocks, as well as a growing range of other organic compounds. Yet, the major drawbacks of these methods for synthesizing biomolecule micro arrays are their low throughput, low degree of automation, low density of target molecules, low yield and batch to batch and process variability. Also, these method are not as miniaturized as the in situ photolithography technique for microarray synthesis.

In short, the current methods of manufacturing micro array rely on serial processing/synthesis of micro arrays using highly customized tool sets such as peptide/DNA synthesizers, spotters, ink jet printers. They involve manual processing operations not amenable to low cost, automated, high throughput, high volume manufacturing.

BRIEF DESCRIPTION OF THE DRAWINGS

FIGS. 1A-F and 1G demonstrate a method for the controllable synthesis of polymers on a solid support involving semiconductor lithography. FIG. 1G is a three-dimensional perspective of solid state synthesis of biomolecules on a microarray.

DETAILED DESCRIPTION

Figure 1A:
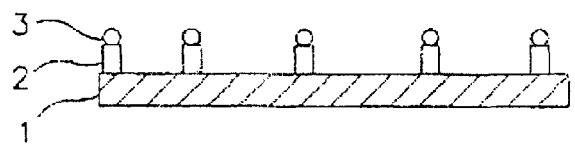

As used in the specification and claims, the singular forms "a", "an" and "the" include plural references unless the context clearly dictates otherwise. For example, the term "an array" may include a plurality of arrays unless the context clearly dictates otherwise.

An "array," "macroarray" or "microarray" is an intentionally created collection of substances, such as molecules, openings, microcoils, detectors and/or sensors, attached to or fabricated on a substrate or solid surface, such as glass, plastic, silicon chip or other material forming an array. The arrays can be used to measure the expression levels of large numbers, e.g., tens, thousands or millions, of reactions or combinations simultaneously. An array may also contain a small number of substances, e.g., a few or a dozen. The substances in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

A "biochip" is a collection of miniaturized test sites (microarrays) arranged on a solid substrate that permits many tests to be performed at the same time in order to achieve higher throughput and speed. Typically, a biochip's surface area is no larger than a fingernail. Like a computer chip that can perform millions of mathematical operations in one second, a biochip can perform thousands of biological reactions, such as decoding genes, in a few seconds. A genetic biochip is designed to "freeze" into place the structures of one or more strands of biological molecule such as DNA, RNA, protein, peptide, etc. Effectively, it is used as a kind of "test tube" for real chemical samples. A specially designed instrument can determine where the sample hybridized with the biological strands in the biochip.

"Substrate," "support" and "solid support" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "analyte," "target" or "target molecule" refers to a molecule of interest that is to be detected and/or analyzed, e.g., a nucleotide, an oligonucleotide, a polynucleotide, a peptide, or a protein. The analyte, target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be a fluorescently labeled antigen, antibody, DNA or RNA. A "bioanalyte" refers to an analyte that is a biomolecule.

The term "capture molecule" refers to a molecule that is immobilized on a surface. The capture molecule generally, but not necessarily, binds to a target or target molecule. The capture molecule is typically an antibody, a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. In the case of a solid-phase immunoassay, the capture molecule in immobilized on the surface of the substrate and is an antibody specific to the target, an antigen, to be detected. The capture molecule may be fluorescently labeled antibody, protein, DNA or RNA. The capture molecule may or may not be capable of binding to just the target molecule or just the probe molecule.

The term "probe" or "probe molecule" refers to a molecule that binds to a target molecule for the analysis of the target. The probe or probe molecule is generally, but not necessarily, has a known molecular structure or sequence. The probe or probe molecule may or may not be attached to the substrate of the array. The probe or probe molecule is typically an antibody, a nucleotide, an oligonucleotide, a polynucleotide, a peptide, or a protein, including, for example, monoclonal antibody, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) In immunoassays, the probe molecule may be a labeled antibody specific to the target, an antigen, to be analyzed. In such case, the capture molecule, the target molecule and the probe molecule form a "sandwich." The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

A "binding partner," refers to a molecule or aggregate that has binding affinity for one or more analytes, targets or other molecules. In this sense, a binding partner is either a "capture molecule" or a "probe molecule." Within the scope of the embodiments of the invention, virtually any molecule or aggregate that has a binding affinity for an analyte or target of interest may be a binding partner, including, but are not limited to, polyclonal antibodies, monoclonal antibodies, single-chain antibodies, chimeric antibodies, humanized antibodies, antibody fragments, oligonucleotides, polynucleotides, nucleic acids, aptamers, nucleic acid ligands and any other known ligand that can bind to at least one target molecule. Although, in certain embodiments a binding partner is specific for binding to a single target, in other embodiments the binding partner may bind to multiple targets that possess similar structures or binding domains.

"Binding" refers to an interaction between two or more substances, such as between a target and a capture or probe molecule, that results in a sufficiently stable complex so as to permit detection of the bound molecule complex. In certain embodiments of the invention, binding may also refer to an interaction between a second molecule and a target.

"Associated with" or "association" refers to a direct or indirect interactions between two or more substances, such as between a target and a capture or probe molecule, that results in a sufficiently stable complex. For example, a molecule or complex of molecules is "associated with" the surface of a substrate when the molecule or complex is either bound to the surface of the substrate directly, through another molecule or substance, or to both. In other words, substances are "associated with" each other when any one member of the substances is directly bound to at least another member of the substances. Additionally, a component of an integrated device is also "associated with" the device. For example, a transistor in an integrated circuit is "associated with" the circuit.

The terms "label," "tag" and "sensor compound" are used interchangeably to refer to a marker or indicator distinguishable by the observer but not necessarily by the system used to identify an analyte or target. A label may also achieve its effect by undergoing a pre-designed detectable process. Labels are often used in biological assays to be conjugated with, or attached to, an otherwise difficult to detect substance. At the same time, Labels usually do not change or affect the underlining assay process. A label or tag used in biological assays include, but not limited to, a radio-active material, a magnetic material, quantum dot, an enzyme, a liposome-based label, a chromophore, a fluorophore, a dye, a nanoparticle, a quantum dot or quantum well, a composite-organic-inorganic nano-cluster, a colloidal metal particle, or a combination thereof.

The terms "die," "polymer array chip," "array," "array chip," or "bio-chip" are used interchangeably and refer to a collection of a large number of capture molecules arranged on a shared substrate which could be a portion of a silicon wafer, a nylon strip or a glass slide. The term "DNA array" or "DNA array chip" is used when the array chip is used to analyze a nucleotide. The term "protein array" is used when the array chip is used to analyze a protein.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components. A chip could be a biochip, for example.

"Micro-Electro-Mechanical System (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either α-, β-, or ω-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

The term "biomolecule" refers to any organic molecule that is part of a living organism. Biomolecules includes a nucleotide, a polynucleotide, an oligonucleotide, a peptide, a protein, a ligand, a receptor, among others. A "complex of a biomolecule" refers to a structure made up of two or more types of biomolecules. Examples of a complex of biomolecule include a cell or viral particles. A cell can include bacteria, fungi, animal mammalian cell, for example.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "polynucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (cDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers.

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogen atoms of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-methyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage or "sugar-phosphate backbone" of the polynucleotide can also be substituted or modified, for instance with methyl phosphonates, O-methyl phosphates or phosphorothioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleosides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including α, β, or ω-amino acids. When the amino acids are α-amino acids, either the L-optical isomer or the D-optical isomer may be used. Additionally, unnatural amino acids, for example, β-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

A "ligand" is a molecule or a portion of a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

A "fluorophore" or "fluorescent compound" can include, but is not limited to, a dye, intrinsically fluorescent protein, lanthanide phosphor, and the like. Dyes, for example, include rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobimane.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "wafer" means a semiconductor substrate. A wafer could be fashioned into various sizes and shapes. It could be used as a substrate for a microchip. The substrate could be overlaid or embedded with circuitry, for example, a pad, via, an interconnect or a scribe line. The circuitry of the wafer could also serve several purpose, for example, as microprocessors, memory storage, and/or communication capabilities. The circuitry can be controlled by the microprocessor on the wafer itself or controlled by a device external to the wafer.

The term "resist" or "photoresist" is an organic or inorganic compound that experiences a change in solubility in a developer solution when exposed to ultraviolet (UV) light. Photoresists used in wafer fabrication are applied to the wafer surface as a liquid or vapor and dried into a film. A resist is used as a thin layer to transfer a circuit pattern to the semiconductor substrate which it is deposited upon. A resist can be patterned via lithography to form a (sub)micrometer-scale, temporary mask that protects selected areas of the underlying substrate during subsequent processing steps. The material used to prepare said thin layer (typically a viscous solution). Resists are generally proprietary mixtures of a polymer or its precursor and other small molecules (e.g. photoacid generators) that have been specially formulated for a given lithography technology. Resists used during photolithography are called photoresists. Photoresists are classified into two groups, positive resists and negative resists. A "positive resist" is a type of photoresist in which the portion of the photoresist that is exposed to light becomes soluble to the photoresist developer and the portion of the photoresist that is unexposed remains insoluble to the photoresist developer. A "negative resist" is a type of photoresist in which the portion of the photoresist that is exposed to light becomes relatively insoluble to the photoresist developer. The unexposed portion of the photoresist is dissolved by the photoresist developer.

Photoresists are most commonly used at wavelengths in the ultraviolet spectrum or shorter (<400 nm). For example, some resists absorb strongly from approximately 300 nm to 450 nm. In the deep ultraviolet (DUV) spectrum, the π-π* electronic transition in benzene (link) or carbon double-bond chromophores (link) appears at around 200 nm. Photoresists can also be exposed by electron beams, producing the same results as exposure by light. One very common positive photoresist used with the I, G and H-lines from a mercury-vapor lamp is based on a mixture of Diazonaphthoquinone (DNQ) and Novolac resin (a phenol formaldehyde resin). DNQ inhibits the dissolution of the novolac resin, however, upon exposure to light, the dissolution rate increases even beyond that of pure novolac. One very common negative photoresist is based on epoxy-based polymer. The common product name is SU-8 photoresist.

Deep Ultraviolet (DUV) resist are typically polyhydroxystyrene-based polymers with a photoacid generator providing the solubility change. However, this material does not experience the diazocoupling. The combined benzene-chromophore and DNQ-novolac absorption mechanisms lead to stronger absorption by DNQ-novolac photoresists in the DUV, requiring a much larger amount of light for sufficient exposure. The strong DUV absorption results in diminished photoresist sensitivity.

Photoresists used in production for DUV and shorter wavelengths require the use of chemical amplification to increase the sensitivity to the exposure energy. This is done in order to combat the larger absorption at shorter wavelengths. Chemical amplification is also often used in electron-beam exposures to increase the sensitivity to the exposure dose. In the process, acids released by the exposure radiation diffuse during the post-exposure bake step. These acids render surrounding polymer soluble in developer. A single acid molecule can catalyze many such 'deprotection' reactions; hence, fewer photons or electrons are needed.

The term "developer" or "photographic developer" is a chemical that reacts with a chemical that has been exposed to light. Positive photoresist developer could be a hydrated alkaline material which dissolves readily in water, giving a buffered alkaline solution for development of novalak polymer films used in micro imaging, for example. Photoresist developer should preferably provide flat trace sidewalls consistently over its useful life, and should be used in automated spray equipment, preferably with pH controlled additions. Some developers are capable of absorbing $CO_2$ from the air and thus lowering its pH. During processing, nitrogen blanket or a floating lid could be used to minimize exposure to air to maintain its effectiveness; fresh developer is generally used with spray systems.

The term "reticle" refers to a transparent, semi-transparent or opaque plate that has a pattern image to be transferred to a photoresist coating on a wafer. A reticle contains the pattern image for only part of the wafer. Reticles are generally used for step-and-repeat steppers and step-and-scan systems for wafer fabrication. A "mask" or "photomask" contains the pattern image for a complete or substantially complete wafer die array and the pattern is usually transferred in a single exposure, typically using 1:1 image transfer methods such as contact aligner, proximity aligner or scanning projection aligner (scanner).

A "protecting group" is a group which is bound to a molecule and designed to block a reactive site in a molecule, but may be removed upon exposure to an activator or a deprotecting reagent. Deprotecting reagents include, for example, acids and bases. Protecting groups can be bound to a monomer, a polymer, a linker molecule or a monomer, or polymer, or a linker molecule attached to a solid support to protect a reactive functionality on the monomer, polymer, or linker molecule.

A "linker" molecule typically is a molecule inserted into the growing polymer that does not necessarily convey functionality to the resulting peptide, such as molecular recognition functionality, but instead elongates the distance between the substrate surface and the peptide functionality to enhance the exposure of the peptide functionality on the surface of the substrate. Preferably a linker should be about 4 to about 40 atoms long to provide exposure. The linker molecules may be, for example, aryl acetylene, ethylene glycol oligomers containing 2-10 monomer units (PEGs), diamines, diacids, amino acids, among others, and combinations thereof. Examples of diamines include ethylene diamine and diamino propane. Alternatively, the linkers may be the same molecule type as that being synthesized (i.e., nascent polymers), such as polypeptides and polymers of amino acid derivatives such as for example, amino hexanoic acids.

A "derivative" is a compound that is formed from a similar compound or a compound that can arise from another compound when one atom or group of atoms are replaced with another atom or group of atoms. In biochemistry, the word "derivative" refers to a compound that can be formed from a precursor compound.

The term "derivatization" refers to a technique used in chemistry which transforms a chemical compound into a product of similar chemical structure, called derivative. Generally, a specific functional group of the compound participates in the derivatization reaction and transforms the educt to a derivate of deviating reactivity, solubility, boiling point, melting point, aggregate state, or chemical composition. Resulting new chemical properties can be used for quantification or separation of the educt. Derivatization techniques are frequently employed in chemical analysis of mixtures and in surface analysis, e.g. in XPS where newly-incorporated atoms label characteristic groups.

Embodiments of the invention relate to system and method of manufacturing biomolecule micro arrays using semiconductor tool sets and associated modules for seamless high throughput, high volume manufacturing of biomolecule micro arrays. The elements of the system and method are: (1) using existing and novel semiconductor manufacturing toolsets towards biomolecule micro array synthesis with high throughput, (2) using a developer module (with puddle development) for coupling building blocks, (3) using hexamethyldisilazane (HMDS) priming module for surface derivatization before coupling the first building block and (4) reducing cycle time enabled by simultaneous usage of multiple modules in the tool sets. The embodiments of the invention addresses the problem of non-availability of methods for seamless, high throughput, high volume synthesis of biomolecule micro arrays.

In the embodiments of the method of manufacturing the biomolecule micro array of the invention include, among others, the following: (1) HMDS prime of the wafer; (2) spin coating of a photoresist on the wafer; (3) soft bake of the spin coated photoresist; (4) exposure of the photoresist to low energy radiation; (5) post-exposure bake of the photoresist; and (6) develop and rinse photoresist.

Table 1 show the processes involved in peptide micro array synthesis as an example indicating the type of module that would be used from a semiconductor toolset for each of the process steps. As shown in Table 1, the surface and attachment chemistries required for surface functionalization with an amine linker can be performed by either liquid phase silanization using a developer module with puddle mechanism for silane/ethanol derivatization followed by spin, wash and rinse with ethanol or vapor phase silanization using a hexamethyldisilazane (HMDS) prime module. The acid coupling steps and the rinse and wash steps can be performed using a developer module with puddle processes.

TABLE 1

Steps and modules for manufacturing the biomolecule micro arrays.

| Step | Peptide array synthesis steps | description of process | Semiconductor module and process equivalent |
|---|---|---|---|
| | *Spacer and attachment chemistry* | | |
| 1 | liquid phase surface functionalization with amine linker | Liquid phase silanziation - Prior cleaned wafer in 3-aminopropyltriethoxysilane (0.5%) in ethanol for 5-30 min - Wash with ethanol | Developer module with puddle mechanism for silane/ethanol derivatization followed by spin - wash and rinse with ethanol |
| | OR | | |
| | vapor phase surface functionalization with amine linker | vapor phase silanization - Appopriate selection of silanes | HMDS prime module |
| 2 | Curing of attachment chemistry | 110 deg. C. for ~5-30 min in N2 environment | Hot plate module (with modification for N2 atmosphere if necessary) |
| 3 | Air cooling at room temperature | ~5 min | Chill plate module |
| | *Amino acid coupling* | | |
| 4 | Building block (amino acid) coupling | Protected amino acid coupled to the amino functionalized surface at 0.1M concentration in a solution containing 0.1M DIC and HOBt (diisopropyl carbodiimide and Hydroxybenzotriazole, activators) in N methyl-2-pyrrolidinone (NMP) for 30 min | Developer module with puddle mechanism for amino acid + activator solution on wafer - Multiple developer modules could be used for the 20 different amino acids or ~4-5 amino acids per module (process optimization could be performed depending on peptide sequence information already available) |
| 5 | Washing | Wash with DCM/DMF (1:1, v/v), DMF, DCM, and DMF, respectively | Could be performed on the rinse step of the same developer module with sequential rinses |
| 6 | Capping of unreacted amine linker groups | 50% acetic anhydride solution in dimethylformamide (DMF) for 30 min | Developer module with puddle mechanism - This process could be performed in the same module as the previous step or decoupled. |
| | *Solid phase deprotection of amino acid protecting groups and neutralization* | | |
| 7 | Photoactive layer spin coating | 2.5% PMMA, 5% PAG, 5% ITX sensitizer in PGMEA. The photosensitive layer was deposited by spin coating at 2000 rpm for 60 sec | Spin coater module |
| 8 | Post-bake | 85 deg. C. for 90 sec | Hot plate module |
| 9 | Cooling | ~2-3 min | Chill plate module |
| 10 | Exposure using manual contact aligner | Dose of 10-50 mJ/cm2 with one mask over the whole wafer | Stepper platform - step and scan with ability to handle multiple reticles OR Maskless lithography using specified pattern CAD files |
| 11 | Strip photoactive layer | Acetone sttrip: Soak in room temp acetone until resist is dissolved (~20 sec). Soak in fresh acetone for a further 1-2 min. DI Water Rinse >3 minutes in running DI water. | Developer module - puddle and rinse functions for acetone strip and DI water rinses |
| 12 | Dry | blow dry with Nitrogen | Spin-dry |
| 13 | Neutralization | 5-10% diisopropylethylamine (DIEA) in DMF for 10 min | Developer module |
| | REPEAT STEPS 2-13 for multiple amino acid coupling using multiple modules | | |

Generally, the first step in the manufacture of the biomolecule microarray of the embodiments of the invention is to clean, dehydrate, and prime the surface of the wafer to promote good adhesion between the photoresist and the wafer surface. Wafer cleaning may involve a wet clean and deionized (DI) water rinse to remove contaminants. Typically, wafer cleaning could be done before the wafer enters the photolithography area. Wafer cleaning involves dehydration dry bake in a closed chamber to drive off most of the adsorbed water on the surface of the wafer and clean and dry the wafer surface. After the dehydration bake, the wafer is primed with HMDS, which acts as an adhesion promoter. The HMDS reacts with the silicon surface of the wafer, which is typically a silicon substrate, to tie up molecular water, while also forming a bond with the resist material, thereby serving as a coupling agent between the silicon and the resist so that these materials become chemically compatible.

HMDS could be applied to the wafer by puddle development in a developer module or by spray or vapor methods in a HMDS spray or vapor prime module. For example, the puddle dispense method could be used for single wafer processing as the temperature and volume of HMDS dispensed could be easily controlled. The puddle dispense method requires a drain and exhaust. The spray dispense and spin method uses a nozzle spray to deposit a fine mist of HMDS on the wafer surface. This method assists in particle removal from the wafer surface.

Vapor Prime Module:

The vapor prime and dehydration bake is the other method for applying HMDS to the wafer surface with a vapor prime coating. The vapor priming could be done at a typical temperature and time of 200 to 250° C. for 30 seconds. An advantage of vapor priming is that there is no contact of liquid HMDS with the wafer, which reduces the possibility of particulate contamination from the liquid HMDS. Vapor priming could also reduce consumption of HMDS. Adequate priming of the wafer surface could be confirmed with a contact angle meter. One variation includes first performing a dehydration bake followed by a vapor prime of single wafers by thermal conduction heating on a hot plate module with nitrogen atmosphere, if necessary. The wafer holder could be made of quartz. The advantages of this variation are inside-out baking of the wafer, low defect density, uniform heating, and repeatability.

Another variation for dehydration bake in conjunction with vapor priming is to use a vacuum chamber with a nitrogen carrier gas. In this process, the wafers are placed in a quartz holder in the oven chamber. The heated chamber could be evacuated and back-filled to a preset pressure with HMDS vapor in the nitrogen carrier gas. At the completion of the pretreatment, the oven could be evacuated and back-filled with nitrogen at atmospheric pressure.

Developer and Rinse Module:

In the embodiments of the invention, the developer and rinse module could be adapted for multiple purposes. For example, the developer module with puddle mechanism could be adapted for liquid phase surface functionalization of a microarray wafer substrate surface with a linker, preferably an amine linker. The developer module could also be adapted for coupling an amino acid to the linker, followed by washing and capping of unreacted amine liner groups. The developer module could also be adapted for the development step to create a pattern in a photoresist on the wafer surface.

During the development step, the soluble areas of the photoresist are generally dissolved by liquid developer chemicals, leaving visible patterns of islands and windows on the wafer surface. In one embodiment, the methods for development are spin, spray, and puddle. Following development, the wafers could be rinsed in DI water and then spin-dried.

Photoresist development preferably uses a liquid chemical developer to dissolve the soluble regions of the resist that were formed during the mask exposure to accurately replicate the reticle pattern in the resist material. The emphasis is on producing CD features that meet the required specifications. If the CDs meet the specifications, then all other features are assumed acceptable since the CD is the most difficult structure to develop.

Positive resist development involves a chemical reaction between the developing solution and the resist to dissolve the exposed resist. The rate at which a developer dissolves the resist is termed the dissolution rate (also referred to as the speed of the developer). A fast dissolution rate is desirable for productivity, but too fast a rate can also be bad for resist performance. Developers also have selectivity. High developer selectivity means the developer reacts quickly with the exposed resist (fast removal rate) relative to the slow reaction with the unexposed resist (slow removal rate). A developer with high selectivity produces sharper and cleaner resist sidewalls, which is desirable for high-density patterning.

Negative resist is crosslinked (hardened) by exposure to UV light. This makes the exposed resist nonsoluble in the developer solution. Generally, little chemical reaction is necessary for negative resist development in the developer solution. This process comprises mainly of a solvent wash of the unexposed resist, which is not crosslinked and therefore soft and soluble. The developer is typically an organic solvent such as xylene that is sprayed on the resist while the wafer is spinning on a vacuum chuck. Developer spray may be followed by another organic solvent sprayed on the wafer to stop the develop process.

In one embodiment of the developer module, a developer is sprayed by a nozzle by scanning across a spinning wafer and the puddle is left on top of the wafer for a specified time. After that, the wafer is spun to remove the developer and another rinse nozzle sprays water/cleaning solution to rinse the wafer. This is called spray and puddle development.

The two preferred techniques to remove exposed resist on spin-coated wafers are: (1) continuous spray development and (2) puddle development.

Continuous Spray Development:

The dissolution of exposed resist with a continuous spray develop tool and solution can be done in a wafer track system after the wafer has completed post-exposure bake. A single wafer could be positioned on a vacuum chuck and spun at a slow speed (e.g., 100 to 500 RPM) while one or more nozzles dispense developer on the resist-coated wafer surface. The developer could be dispensed in a fine mist, with some processes using ultrasonic atomization to allow for low-velocity dispersion. A low velocity exit minimizes adiabatic (constant heat transfer) cooling effects during dispense, where the temperature of the developer drops due to its expansion from a high pressure region to a low pressure region. The nozzle design may require a heating system for the developer to minimize the cooling effect. The nozzle spray pattern and speed of the wafer rotation help to achieve repeatability in the resist dissolution rate and uniformity across the wafer.

Puddle Development:

In the puddle develop approach a small amount of developer is dispensed onto the wafer and forms a puddle that has a puddle meniscus over the entire wafer. Excessive developer should be avoided to minimize backside wafer wetting. The wafer can be stationary or slowly rotating on a heated chuck. There could be variations as to whether the wafer is static or rotating after the initial developer is formed as a puddle on the wafer. In all cases, the developer is left on the resist for sufficient time to allow the soluble resist areas to become completely dissolved. As an example, a multiple-puddle method is used where the first puddle is left on the wafer for a predetermined time (such as 10 to 30 seconds, depending on the type of developer). It is then spun off and a new puddle is dispensed and left on the wafer for a defined time. This second puddle replenishes the developer chemicals and rejuvenates the chemical reaction between the developer and the resist. It is also possible to spray the developer onto the wafer during the second puddle application.

Spin Coat Module:

The wafer could be coated with the liquid photoresist material by a spin coating method. In one embodiment, the wafer could be mounted on a vacuum chuck, which is a flat metal or Teflon disc that has small vacuum holes on its surface to hold the wafer. A precise amount of liquid photoresist is applied to the wafer and then the wafer is spun to obtain a uniform coating of resist on the wafer. Different resists could require different spin coating conditions, such as an initial slow spin (e.g., 500 rpm), followed by a ramp up to a maximum rotational speed of 3,000 rpm or higher. Some of the variables for photoresist application are time, speed, thickness, uniformity, particulate contamination, and resist defects such as pinholes.

Soft Bake Module:

After the resist has been applied to the wafer surface, it undergoes a soft bake (shown as step 8 "Post-bake" in Table 1) to drive off most of the solvent in the resist. The soft bake process promotes adhesion and uniformity on the wafer. In one embodiment, the soft bake temperatures could be 85 to 120° C. for 30 to 60 seconds, preferably at 90 to 100° C. for 30 seconds on a hot plate, followed by a cooling step on a chill plate module to achieve wafer temperature control for uniform resist characteristics.

One method for resist soft bake is heat conduction from a wafer on a vacuum hot plate module. In this method, heat is quickly conducted from the hot plate through contact with the backside of the wafer to the resist. The resist is heated from the wafer-resist interface outward, which minimizes the potential for solvent entrapment. Because of the short cycle time (e.g., 30 to 60 seconds), this single-wafer hot plate method is suitable for the flow of multiple wafers through the process steps of an automated wafer track system. In the wafer track process now, the heating is followed by cooldown step on a chill plate or cooling plate module. This step rapidly cools the wafer for the next operation. The vacuum hot plate module design could be of the same type as that used for dehydration bake module. Optionally, infrared (IR), microwave, and convection heating could be used for soft bake.

Alignment and Exposure Module:

In the alignment and exposure module, a mask is aligned to the correct location of the resist-coated silicon wafer. The wafer surface could be bare silicon but could also have an existing pattern previously defined on its surface. Once aligned, the mask and wafer are exposed to controlled radiant light (typically UV light) to transfer the mask image to the resist-coated wafer. The light energy activates the photosensitive components of the photoresist. Preferred quality measures for alignment and exposure include: line width resolution, overlay accuracy, and particles and defects.

The aligner could be contact aligner, proximity aligner, scanning projection aligner (scanner), step-and-repeat aligner (stepper), and step-and scan system. The contact aligner could be used for line widths of about 5 microns, and as thin as 0.4 microns. The mask for the contact aligner has the complete array of all die patterns to be photographed on the wafer surface. After the wafer is coated with the photoresist, the mask pattern is aligned and brought into direct contact on with the resist coating on the wafer. At this time, the wafer and mask are exposed to UV rays. The proximate aligner is suitable for line width of 2 to 4 microns. In proximity alignment, the mask contains the entire wafer pattern, but it does not make direct contact with the resist. Instead, the mask is positioned in close contact with the resist surface. The scanning projection aligner projects a full wafer mask with a 1:1 image onto the wafer surface using a mirror system (i.e., based on reflective optics).

The step-and-repeat aligner (stepper) projects one exposure field (which may be one or more chips, including biochips, on the wafer), then steps to the next location on the wafer to repeat the exposure. Steppers can create critical dimensions of 0.35 microns with i-line photoresist and 0.25 microns with deep UV (DUV) photoresists. A stepper generally uses a reticle, which contains the pattern in an exposure field corresponding to one or more die. A mask is generally not be used in a stepper since a mask contains the entire die matrix. The optical projection exposure system of steppers generally has refractive optics to project the reticle image onto the wafer.

An advantage of optical steppers is their ability to use a reduction lens. Traditionally, i-line stepper reticles are sized 4×, 5×, or 10× larger than the actual image to be patterned. To further explain the purpose of a reduction lens, a stepper with a 5× reticle requires a 5:1 reduction lens to transfer the correct image size to the wafer surface. This demagnification factor makes it easier to fabricate the reticle because the features on the reticle are five times larger than the final image on the wafer.

At each step in the exposure process, the stepper would focus the wafer and the reticle to the projection lens, align the wafer to the reticle, expose the resist with UV light that passes through the transparent regions of the reticle, and then step to the next location on the wafer to repeat the entire sequence. By following this process, the stepper would ultimately transfer the full die array onto the wafer in a sequence of exposure steps. Because the stepper exposes only a small portion of the wafer at one time, compensations for variations in wafer flatness and geometry can be easily performed.

Steppers could use conventional mercury arc lamp illumination sources (for g-line of 436 nm, h-line of 405 nm, and i-line of 365 nm) with a critical dimension (CD) to 0.35 microns. To obtain a 248 nm DUV wavelength source, the mercury arc lamp source is replaced with a KrF (kryptonfluoride) excimer laser. This equipment permits patterning 0.25 microns critical dimensions.

The step-and-scan system is an optical lithography system that combines the technology from scanning projection aligners and step-and-repeat steppers by using a reduction lens to scan the image of a large exposure field onto a portion of the wafer. A focused slit of light is scanned simultaneously across the reticle and wafer. Once the scan and pattern transfer is completed, then the wafer is stepped to the next exposure field and the process is repeated.

Post-Exposure Bake Module:

The post-exposure bake could be on a hot plate at 100 to 110° C. for the DUV resists. This bake follows the photoresist exposure. It could be an optional step for non-DUV conventional resists.

After the wafer with exposed resist exits the exposure system, it enters the wafer track system and undergoes a short post-exposure bake (PEB) step. A thermal PEB is useful for chemically amplified DUV resists for catalyzing resist chemical reactions. For conventional i-line resists based on DNQ chemistry, PEB is done to improve adhesion and reduce standing waves. Resist manufacturers include recommended time and temperature specifications for PEB in their product literature.

During PEB, the exposed regions of a chemically amplified DUV resist become soluble in the developer. A chemically amplified DUV resist, a protecting chemical (e.g., t-BOC) makes the resist insoluble in the developer. During UV exposure, a photoacid generator (PAG) generates an acid in the exposed regions. To make the exposed resist soluble to the developer, the post-exposure bake (PEB) heats the resist, which causes the acid-catalyzed deprotection reaction to occur. The acid removes the protecting group from the resin and the exposed resist is now soluble in the developer solution. PEB is a preferred step in resist processing for chemically amplified DUV resists.

Hard Bake Module:

A post-development thermal bake, referred to as hard bake, is optional and could be used to evaporate the remaining photoresist solvent and improve the adhesion of the resist to the wafer surface. This step could stabilize the resist for the following etch or implant processing. The hard bake temperature for positive resists could be about 120 to 140° C.

Development Inspection Module:

After the resist is patterned on the wafer, an inspection could be undertaken to verify the quality of the resist pattern. The inspection system could be manual or preferably automated for patterning on highly integrated layers. The inspection could identify wafers that have quality problems with the resist and characterize the performance of the photoresist process to meet specifications. If the resist is defective, it could be removed through resist stripping and the wafer could be reprocessed.

The technical advantages of the embodiments of this invention are: (1) High throughput by combination of multiple modules and links for batch processing; (2) Superior, proven process control through highly automated instrumentation adapted from the semiconductor industry; (3) Amenability to large number of process steps (hundreds to thousands) required for biomolecule micro array synthesis; (4) Established statistical process control (SPC) procedures to enable standardization and quality control (six-sigma) of biomolecule micro arrays; (5) Improvement in yield (process, die and wafer levels) and reliability of micro array synthesis; and (6) Minimum exposure to atmosphere increasing the yield and reliability of synthesis of biomolecules.

The semiconductor equipment, includes coater/developers, dry etchers, thermal processing systems, single wafer deposition systems, wet cleaning systems, ion implantation systems, test systems, and advanced defect inspection and metrology software. The semiconductor process typically starts with a silicon wafer which is cleaned to remove organic and inorganic contaminants. Wafers are placed into a furnace and heated to a preset temperature and exposed to a flow of gas to form a dielectric film such as that of silicon dioxide on the wafer surface. Using a CVD (Chemical Vapor Deposition) or oxidation process, a very thin layer of dielectric material is deposited onto the wafer surface. This dielectric layer is used as the insulating material between devices such as transistors formed on the wafer. In many areas of the wafer fabrication process, wafers are heated to extremely high temperatures in a short amount of time, in order to improve the functionality of the devices.

Then while wafers are rotated at a high speed in a coater, they are coated with a uniform film of photoresist, which is a light sensitive material. Subsequently, a mask with a pattern is aligned with the wafer and radiation (typically UV light) is applied to transfer the pattern to the photoresist using a stepper. Next, the photoresist that is either exposed or unexposed is removed by developing the photoresist in a developer. For example, in the developer, the wafer is uniformly covered with a developing solution to develop the mask patterns. With positive photoresist, the portion of the resist that has been exposed to light becomes soluble, thus leaving the mask patterns on the wafer surface. With negative photoresist, the portion of the resist that has not been exposed to light becomes soluble, thus leaving the mask patterns on the wafer surface. The process resist coating, exposure and developing is called the photolithography process.

In one embodiment, the photolithography process is similar to creating photographic prints in which a microscopic circuitry pattern is projected onto the wafer that has been coated with a light-sensitive chemical. Like camera film, the wafer is then developed, leaving behind a stenciled pattern of photoresist to define the areas on the wafer that will be affected by the remaining steps in the transistor cycle. The photoresist is deposited by spin-coater/developers. This process is repeated—and a new circuitry pattern is used—each time another layer of the chip is built.

The semiconductor process could further include the following steps, which may or may not be part of the embodiments of the invention. A plasma dry etch step to strip the dielectric film in accordance with the patterns developed on the photoresist. Plasma etching occurs when the photoresist film is patterned onto the wafer, and the pattern is transferred to the film below. Within an etch chamber, highly reactive plasma gasses react with the wafer to remove the film where the pattern leaves it exposed. Once complete, the wafer has a dielectric film with a pattern that is ready to receive tungsten or copper, which serves as an interconnection to the next layer.

The portion protected by the photoresist remains intact, thus preserving the original film structure of the dielectric film under the photoresist. Then, the remaining photoresist could be removed. Then, a gate electrode could be formed by repeating the photolithography process and etching. The gate electrode could be deposited on top of a gate dielectric, thus forming a connection point between a transistor switch and subsequent wiring. Then, ion implantation could be used to dope or implant the surface of the wafer with known quantity of impurities, such as boron or arsenic. Sacrificial films are used to prevent ions from implanted in unwanted areas of the wafer. Subsequently, annealing could be used to diffuse the impurities to a more uniform density. Subsequently, interlayer dielectric film is deposited to insulate the devices such as transistors and wires. The deposition technique may use a chemical vapor deposition (CVD) system that accumulates gaseous materials through chemical reactions or using a coater that applies liquid materials through spinning. The interlayer dielectric film is etched from areas other than where it is required to insulate the devices such as transistors and wires. Next a vapor deposition system is used to deposit metal film to form wiring. The above steps would typically complete the integrated circuit (IC) chip or microarray making process. Note that each wafer could contain hundreds of IC chips or micro arrays, which could be identical or different. By the embodiments of invention, the plurality of the IC chips or micro arrays could be simultaneously made on a wafer. The finished wafer could be cut into IC chips or micro arrays, which then can be packaged to the complete the manufacture of individual IC chip or microarray.

The semiconductor toolsets within the embodiments of the invention include lithography equipment including tracks and steppers. These enable automation of standard processes such as spin coating, bake processes, development and exposure. The track could be enclosed inside an enclosure where the temperature and humidity can be controlled. Also the air could be filtered using special filters that filters ozone that is not conducive to DNA/peptide synthesis.

Examples of the track systems are TOKYO ELECTRON's CLEAN TRACK coater/developer systems for 200 mm and 300 mm high volume production and 193 nm photolithography processing and beyond. Based on the same platform used for lithographic coating and developing, CLEAN TRACK also offers spin-on-dielectric solutions with inline cure processing.

Each process step within these track systems is called a module. For example, the spin-coater where the resist is coated on to the wafer is called the spin-coater module. An example of a spin-coater is the TRACTIX spin tool, which is a stand alone, small-footprint track system designed for the spin deposition of photoresist, developer, polymer and other materials common to integrated circuit photolithography. Similarly, there are hotplate modules, chill plate modules and developer modules. Steppers are exposure tools that have excellent accuracy, alignment and dose uniformity that can perform multiple lithography systems. Examples include Nikon and ASML systems.

The embodiments of the invention use semiconductor processing tools including multiple links with the associated different modules for high throughput, high density bio molecule micro array synthesis. Link refers to the system wherein the track system is linked to the stepper exposure system via a robotic arm such that wafers coming out of a module in the track can then be sent to the stepper exposure system and then brought be back to the track for further processing such as development. Typically lithography is performed as part of a well-characterized module, which includes the wafer surface preparation, photoresist deposition, alignment of the mask and wafer, exposure, develop and appropriate resist conditioning. The standard steps found in a lithography module are (in sequence): dehydration bake, HMDS prime, resist spin/spray, soft bake, alignment, exposure, post exposure bake, develop hard bake and de-scum. Not all lithography modules will contain all the process steps. The modules in the track could be controlled by robotics and precision process control such that times spent in the modules and the parameters for each module (temperature, spin speed, etc.) are extremely well controlled.

In the embodiments of the invention, existing track systems that are linked to the stepper platform can also be adapted for use in a seamless fashion for biomolecule array synthesis. This could be possible as there could be a one-to-one relationship of what a module would be typically used in the track system for IC chip manufacturing and could be used for biomolecule microarray synthesis as explained in context of Table 1 discussed in the Example section.

Embodiments of the present invention provide methods for the synthesis of polymers on a solid support using photolithographic technology. Polymer synthesis according to embodiments of the invention can be accomplished with precision and can therefore be used to provide controlled-density micro arrays. Since the lithographic methods of the present invention are general for a variety of polymer synthesis reactions, micro arrays can be created that are comprised of nucleic acids, peptides, and or other organic polymeric molecules.

The embodiments of the invention include the use of a new photoactive layer formulation requiring very low energy (10-50 mJ/cm$^2$) for photo acid generation and deprotection of the t-BOC protecting group. This low exposure dose requirement enables the use of stepper platforms currently in use for semiconductor processing for biomolecule array synthesis. By the use of the specifically designed formulations for the photoresist, the dose required for deprotection of the protected amino acid was reduced as explained below in greater details. Hence steppers that typically deliver 10s of mJ/cm$^2$ of exposure could be used.

Figure 1B:
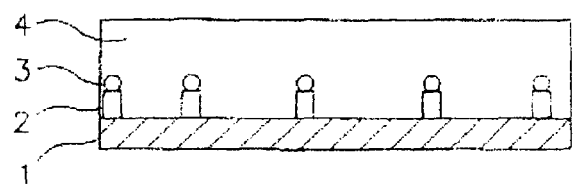
Figure 1C:
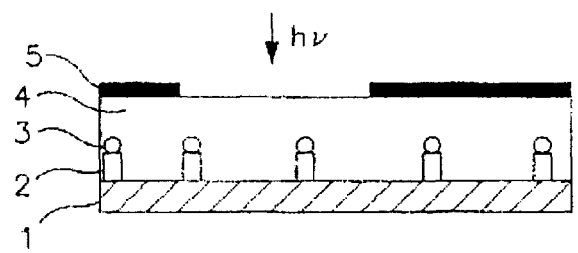
Figure 1D:
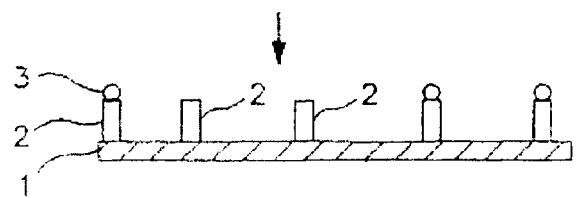
Figure 1E:
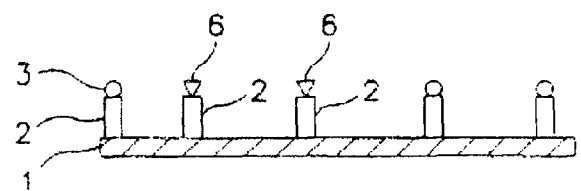
Figure 1G:
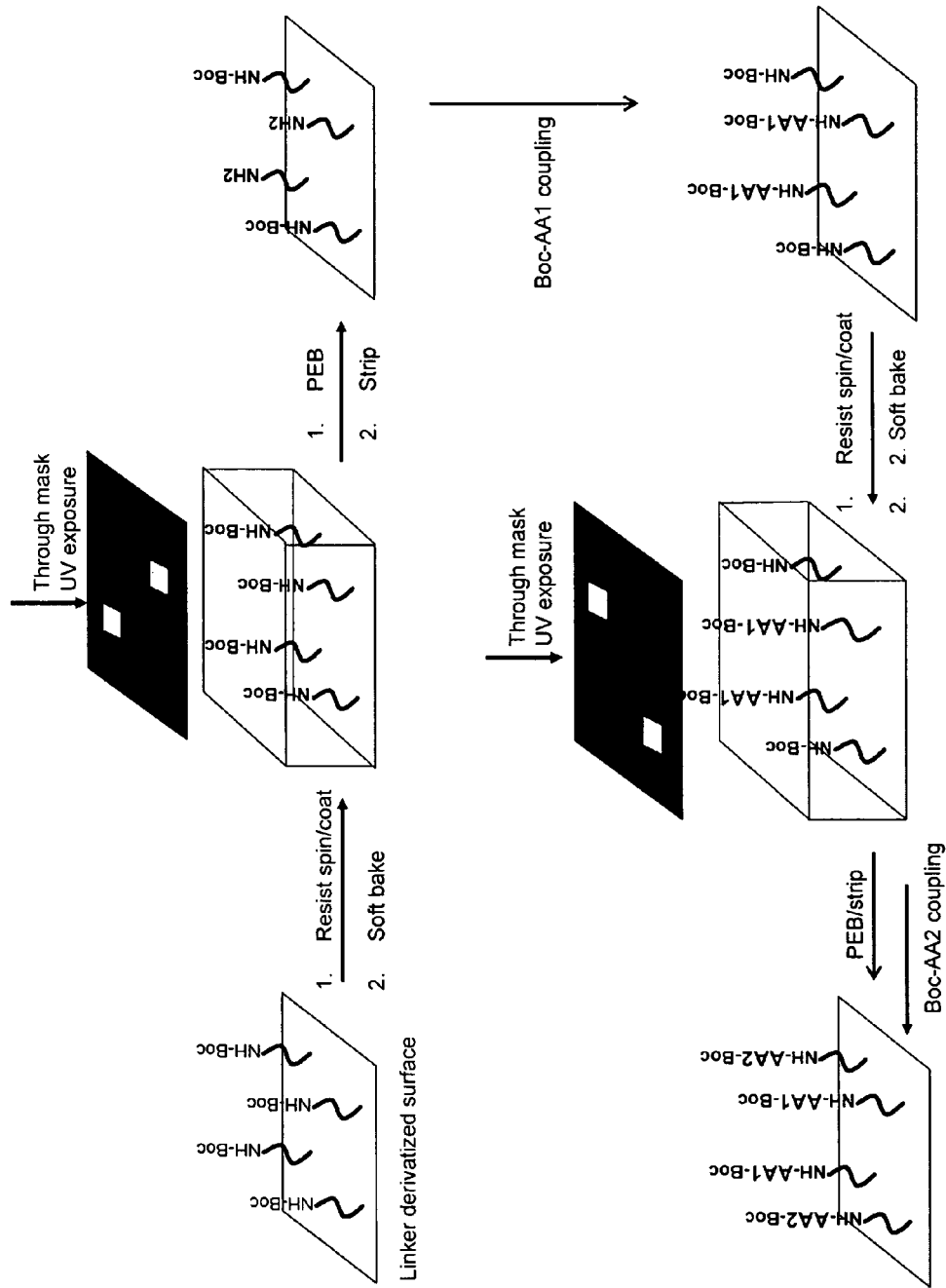

A method for synthesizing polymers within one or more selected region(s) of a solid support is shown in FIGS. 1A through 1E and 1G. In particular, FIG. 1G is a three-dimensional perspective of solid state synthesis of biomolecules on a microarray, which is described in the examples of this application. In general, the method includes attachment of a first building block molecule 2, for example, an amino acid or linker (or spacer) molecule, to the surface of a substrate 1. Additionally, mixtures of different building blocks 2 may also be used. For example, in FIG. 1A a first building block 2 can be an amino acid that is attached to a substrate 1 that is comprised of amino-functionalized glass, through the formation of a peptide bond between the carboxylate of the amino acid and the amine group of the glass. The terminal bond-forming site of the building block 2 is protected with a protecting group 3. For example, the α-amino group of an amino acid can be protected with an N-protecting group 3 to prevent unwanted reactivity. If necessary, a side chain of the building block (for example, an R group of an amino acid) may also have a protecting group. Suitable protecting groups include, for example, t-butoxycarbonyl (t-BOC) (FIG. 2, structure (II)), 2-(4-biphenylyl)-2-oxycarbonyl, and fluorenyl-methoxycarbonyl (FMOC) (FIG. 2, Structure (III)). Advantageously, embodiments of the present invention are not limited to the type of acid- or base-removable protective group or building block selected.

Referring now to FIG. 1B, once the first polymer building block has been attached to a substrate, a layer of photoresist 4 is deposited over the substrate 1 surface. In embodiments of the invention, the photoresist layer can be created from a solution comprising a polymer, a photosensitizer, and a photo-active compound or molecule in a solvent. The photoresist can be applied using any method known in the art of semiconductor manufacturing for the coating of a wafer with a photoresist layer, such as for example, the spin-coating method. The photoresist-coated substrate is then baked to remove excess solvent from the photoresist for film uniformity.

In FIG. 1C, a photomask 5 (the photomask can be a physical mask or any other source capable of projecting pattern image on the surface, for example, a micro-mirror) is applied over photoresist layer 4. The photomask 5 may be applied using standard techniques and materials used in the semiconductor fabrication industry. For example, the photomask 5 may be a transparent pane, such as a quartz pane, having an emulsion or metal film on a surface creating the mask pattern. Suitable metals include chromium. The pattern of the mask is chosen so that regions on the surface of the substrate can be selectively activated for polymer synthesis. Radiation, for example, ultra violet radiation (UV) or deep ultraviolet radiation (DUV), may then be directed through the photomask 5 onto the photoresist layer. The photoresist 4 is exposed in those regions of the mask that are transparent to the impinging radiation. In general, the device used for creating a pattern in the photoresist can be a physical mask or any other source capable of projecting a pattern image, for example a micro-mirror.

The exposure of the photoresist 4 to radiation generates cleaving reagents (species that catalyze the removal of a protective group, for example) in the exposed portion of the photoresist layer 4. The generation of cleaving reagents in the photoresist may be the result of a number of processes. For example, the cleaving reagent may result from the direct radiation-induced decomposition of or chemical transformation of a photoactive cleavage reagent precursor compound. Alternatively or in addition, generation of the cleaving reagent may occur through the absorption of light by a photosensitizer followed by reaction of the photosensitizer with the cleavage reagent precursor, energy transfer from the photosensitizer to the cleavage reagent precursor, or a combination of two or more different mechanisms.

As a result of the radiation-induced generation of the cleaving reagent (catalyst), the protecting groups 3 are cleaved from the molecules 2 under the exposed area(s) of the photoresist. The molecules 2 located under the unexposed masked regions remain unreacted. The cleaving process leading to the removal of the protecting groups 3 may, for example, be acid-catalyzed cleavage or base-catalyzed cleavage. The chemistry of the process will depend on the type of protecting groups 3 and on the type of cleaving reagents that are generated in the photoresist upon radiation exposure. For example, if the protecting group 3 is t-BOC, acid cleavage can be used. Acids may be generated in the photoresist, for example, through the exposure of sulfonium or halonium salts to radiation (FIG. 2, Structures (IV-VII) and (VIII-IX), respectively). If the protecting group is FMOC, for example, then base cleavage can be used. Cleavage can be accomplished through the reaction of a photogenerated amine or diamine through a decarboxylation process. The rate of protecting group removal can be accelerated by heating the substrate after the exposure to radiation (post exposure bake). The post exposure bake (PEB) serves multiple purposes in photoresist processing. First, the elevated temperature of the bake drives diffusion of the photoproducts. A small amount of diffusion can be useful in minimizing the effects of standing waves, periodic variations in exposure dose throughout the depth of the film that result from interference of incident and reflected radiation. Another purpose of the PEB is to drive the acid-catalyzed reaction. Chemical amplification is important because it allows a single photoproduct to cause many solubility-switching reactions, thus increasing the sensitivity of these photoresist systems.

Subsequent to the exposure of the masked substrate to radiation, the photoresist is removed. The photoresist layer 4 may be removed using acetone or another similar suitable solvent. The resulting surface-modified substrate is shown schematically in FIG. 1D. In this structure, there are three regions shown: two regions that have protected molecules and a region having deprotected molecules. The deprotected molecules are available for further reaction, such as for example, a peptide-bond forming coupling reaction whereas the molecules that retain their protective groups are not available for further reaction. Solid phase peptide synthesis can be carried out using standard techniques well-known in the art. FIG. 1E shows a structure resulting from the reaction of the deprotected surface-attached molecules. In FIG. 1E, a building block 6 has been added to molecule 2. Building block 6 may be the same or different from molecule 2. The building block 6 is protected with a protecting group to prevent unwanted reactions.

The processes illustrated in FIGS. 1A-E may be repeated to form polymers on the substrate surface. Through the selection of different mask configurations, different polymers comprising building blocks 2 and 6-10 may be formed in regions upon the surface. In the case where the building blocks are amino acids, peptides having the same or different known sequences are formed in known regions on the surface of the substrate. In general, polymers containing from about 2 to about 50 mers (polymeric units) can be created. In embodiments of the invention peptides having a length of about 6 to about 20 amino acids are created.

Any unreacted deprotected chemical functional groups may be capped at any point during a synthesis reaction to avoid or to prevent further bonding at such molecule. In general, capping reagents can be a reagent that prevents further reactivity at the site of polymer chain formation. Capping groups cap deprotected functional groups by, for example, binding with the unreacted amino functions to form amides. Capping agents suitable for use in an embodiment of the invention include: acetic anhydride, n-acetylimidizole, isopropenyl formate, fluorescamine, 3-nitrophthalic anhydride and 3-sulfoproponic anhydride.

Figure 2:
FIG. 2 I-XIII provides chemical structure diagrams for exemplary molecules and functional groups.
Figure 2:
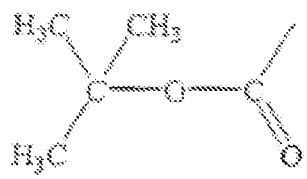
Figure 2:
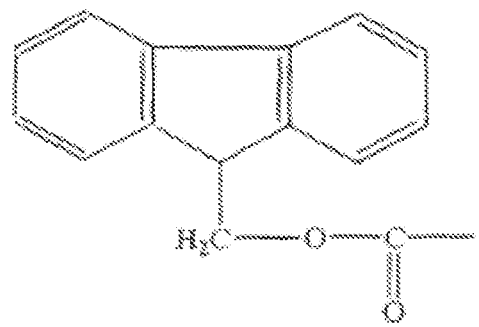
Figure 2:
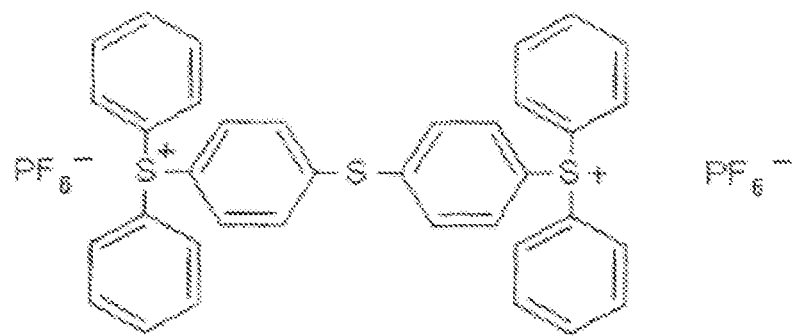
Figure 2:
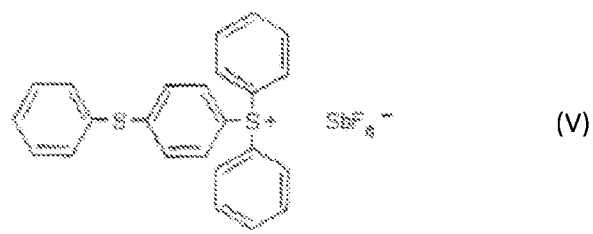
Figure 2:
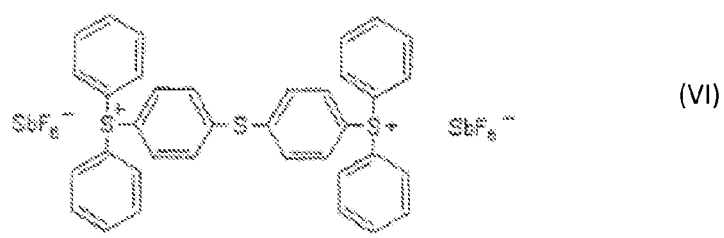
Figure 2:
Figure 2:
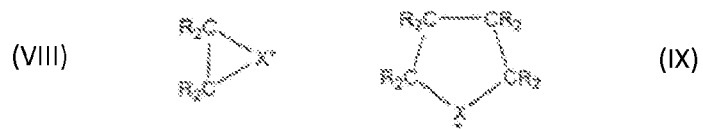
Figure 2:
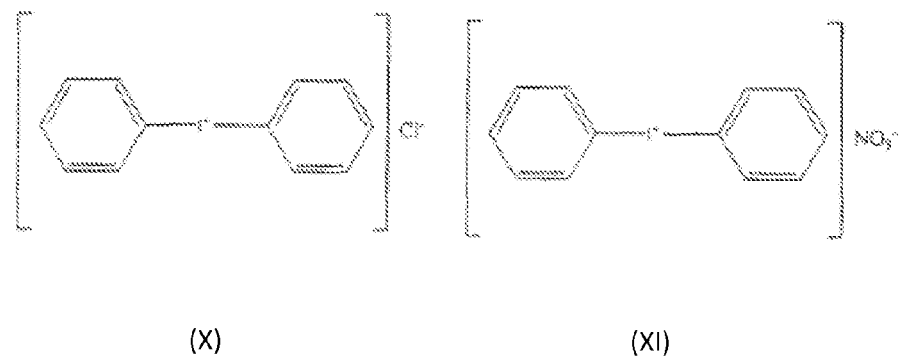
Figure 2:
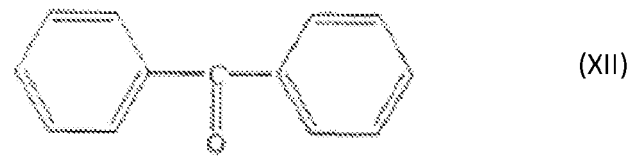
Figure 2:
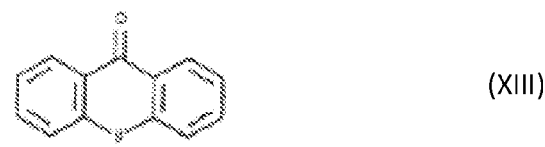

FIG. 2, Structure (I), shows a general structural representation for an amino acid. In general, an amino acid contains an amine group, a carboxylic group, and an R group. The R group can be a group found on a natural amino acid or a group that is similar in size to a natural amino acid R group. Additionally, unnatural amino acids, for example, β-alanine, phenylglycine, homoarginine, aminobutyric acid, aminohexanoic acid, aminoisobutyric acid, butylglycine, citrulline, cyclohexylalanine, diaminopropionic acid, hydroxyproline, norleucine, norvaline, ornithine, penicillamine, pyroglutamic acid, sarcosine, and thienylalanine are also contemplated by the embodiments of the invention. These and other natural and unnatural amino acids are available from, for example, EMD Biosciences, Inc., San Diego, Calif.

Protective groups that may be used in accordance with an embodiment of the invention include all acid and base labile protecting groups. For example, peptide amine groups are preferably protected by t-butoxycarbonyl (t-BOC or BOC) (shown in FIG. 2, Structure (II)) or benzyloxycarbonyl (CBZ), both of which are acid labile, or by 9-fluorenyl-methoxycarbonyl (FMOC) (shown in FIG. 2, Structure (III)), which is base labile.

Additional protecting groups that may be used in accordance with embodiments of the invention include acid labile groups for protecting amino moieties: tert-amyloxycarbonyl, adamantyloxycarbonyl, 1-methylcyclobutyloxycarbonyl, 2-(p-biphenyl)propyl(2)oxycarbonyl, 2-(p-phenylazophenyl)propyl(2)oxycarbonyl, .alpha.,.alpha.-dimethyl-3,5-dimethyloxybenzyloxy-carbonyl, 2-phenylpropyl(2)oxycarbonyl, 4-methyloxybenzyloxycarbonyl, furfuryloxycarbonyl, triphenylmethyl(trityl), p-toluenesulfenylaminocarbonyl, dimethylphosphinothioyl, diphenylphosphinothioyl, 2-benzoyl-1-methylvinyl, o-nitrophenylsulfenyl, and 1-naphthylidene; as base labile groups for protecting amino moieties: 9-fluorenylmethyloxycarbonyl, methylsulfonylethyloxycarbonyl, and 5-benzisoazolylmethyleneoxycarbonyl; as groups for protecting amino moieties that are labile when reduced: dithiasuccinoyl, p-toluene sulfonyl, and piperidino-oxycarbonyl; as groups for protecting amino moieties that are labile when oxidized: (ethylthio)carbonyl; as groups for protecting amino moieties that are labile to miscellaneous reagents, the appropriate agent is listed in parenthesis after the group: phthaloyl(hydrazine), trifluoroacetyl (piperidine), and chloroacetyl (2-aminothiophenol); acid labile groups for protecting carboxylic acids: tert-butyl ester; acid labile groups for protecting hydroxyl groups: dimethyltrityl.

Solid support, support, and substrate could be any material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain embodiments, the solid support may be porous.

Substrate materials useful in embodiments of the present invention include, for example, silicon, bio-compatible polymers such as, for example poly(methyl methacrylate) (PMMA) and polydimethylsiloxane (PDMS), glass, $SiO_2$ (such as, for example, a thermal oxide silicon wafer such as that used by the semiconductor industry), quartz, silicon nitride, functionalized glass, gold, platinum, and aluminum. Functionalized surfaces include for example, amino-functionalized glass, carboxy functionalized glass, and hydroxy functionalized glass. Additionally, a substrate may optionally be coated with one or more layers to provide a surface for molecular attachment or functionalization, increased or decreased reactivity, binding detection, or other specialized application. Substrate materials and or layer(s) may be porous or non-porous. For example, a substrate may be comprised of porous silicon.

Photoresist formulations useful in the present invention include a polymer, a solvent, and a radiation-activated cleaving reagent. Useful polymers include, for example, poly(methyl methacrylate) (PMMA), poly-(methyl isopropenyl ketone) (PMPIK), poly-(butene-1-sulfone) (PBS), poly-(trifluoroethyl chloroacrylate) (TFECA), copolymer-(α-cyano ethyl acrylate-α-amido ethyl acrylate) (COP), and poly-(2-methyl pentene-1-sulfone). Useful solvents include, for example, propylene glycol methyl ether acetate (PGMEA), ethyl lactate, and ethoxyethyl acetate. The solvent used in fabricating the photoresist may be selected depending on the particular polymer, photosensitizer, and photo-active compound that are selected. For example, when the polymer used in the photoresist is PMMA, the photosensitizer is benzophenone, and the photoactive compound is diphenyliodonium chloride, PGMEA or ethyl lactate may be used as the solvent.

In exemplary photoresist formulations, the mass concentration of the polymer may between about 5% and about 50%, the mass concentration of a photosensitizer may be up to about 20%, the mass concentration of the photo-active compound may be between about 1% and 10%, the balance comprising a suitable solvent. After the photoresist is deposited on the substrate, the substrate typically is heated to form the photoresist layer. Any method known in the art of semiconductor fabrication may be used to for depositing the photoresist solution. For example, the spin coating method may be used in which the substrate is spun typically at speeds between about 1,000 and about 5,000 revolutions per minute for about 30 to about 60 seconds. The resulting wet photoresist layer has a thickness ranging between about 0.1 µm to about 2.5 µm.

Catalysts for protective group removal (also referred to as cleaving reagents) useful in the present invention include acids and bases. For example, acids can be generated photochemically from sulfonium salts (FIG. 2, Structures IV-VII), halonium salts (FIG. 2, Structures VIII-IX), and polonium salts (FIG. 2, Structures X-XI). Sulfonium ions are positive ions, $R_3S^+$, where R is, for example, a hydrogen or alkyl group, such as methyl, phenyl, or other aryl group. Trimethyl sulfonium iodide and triaryl sulfonium hexafluoroantimonatate (TASSbF$_6$) are shown in FIG. 2, Structures VII and VI, respectively. In general, halonium ions are bivalent halogens, $R_2X^+$, where R is a hydrogen or alkyl group, such as methyl, phenyl, or other aryl group, and X is a halogen atom. The halonium ion may be linear or cyclic. Polonium salt refers to a halonium salt where the halogen is iodine, the compound $R_2I^+Y^-$, where Y is an anion, for example, a nitrate, chloride, or bromide. FIG. 2 shows diphenyliodonium chloride and diphenyliodonium nitrate (Structure X and XI, respectively).

Photogenerated bases include amines and diamines having photolabile protecting groups.

Optionally, the photoresists useful in the present invention may also include a photosensitizer. In general, a photosensitizer absorbs radiation and interacts with the cleavage reagent precursor, through one or more mechanisms, including, energy transfer from the photosensitizer to the cleavage reagent precursor, thereby expanding the range of wavelengths of radiation that can be used to initiate the desired catalyst-generating reaction. Useful photosensitizers include, for example, benzophenone (FIG. 2, Structure XII) and other similar diphenyl ketones, thioxanthenone (FIG. 2, Structure XIII), isopropylthioxanthenone, anthraquinone, fluorenone, acetophenone, and perylene. Thus, the photosensitizer allows the use of radiation energies other than those at which the absorbance of the radiation-activated catalyst is non-negligible.

A catalytic enhancer is a compound or molecule that is added to a photoresist in addition to a radiation-activated catalyst. A catalytic enhancer is activated by the catalyst produced by the radiation-induced decomposition of the radiation-activated catalyst and autocatalyticly reacts to further (above that generated from the radiation-activated catalyst) generate catalyst concentration capable of removing protecting groups. For example, in the case of an acid-generating radiation-activated catalyst, the catalytic enhancer is activated by acid and or acid and heat and autocatalyticly reacts to form further catalytic acid, that is, its decomposition increases the catalytic acid concentration. The acid produced by the catalytic enhancer removes protecting groups from the growing polymer chain.

Figure 3:
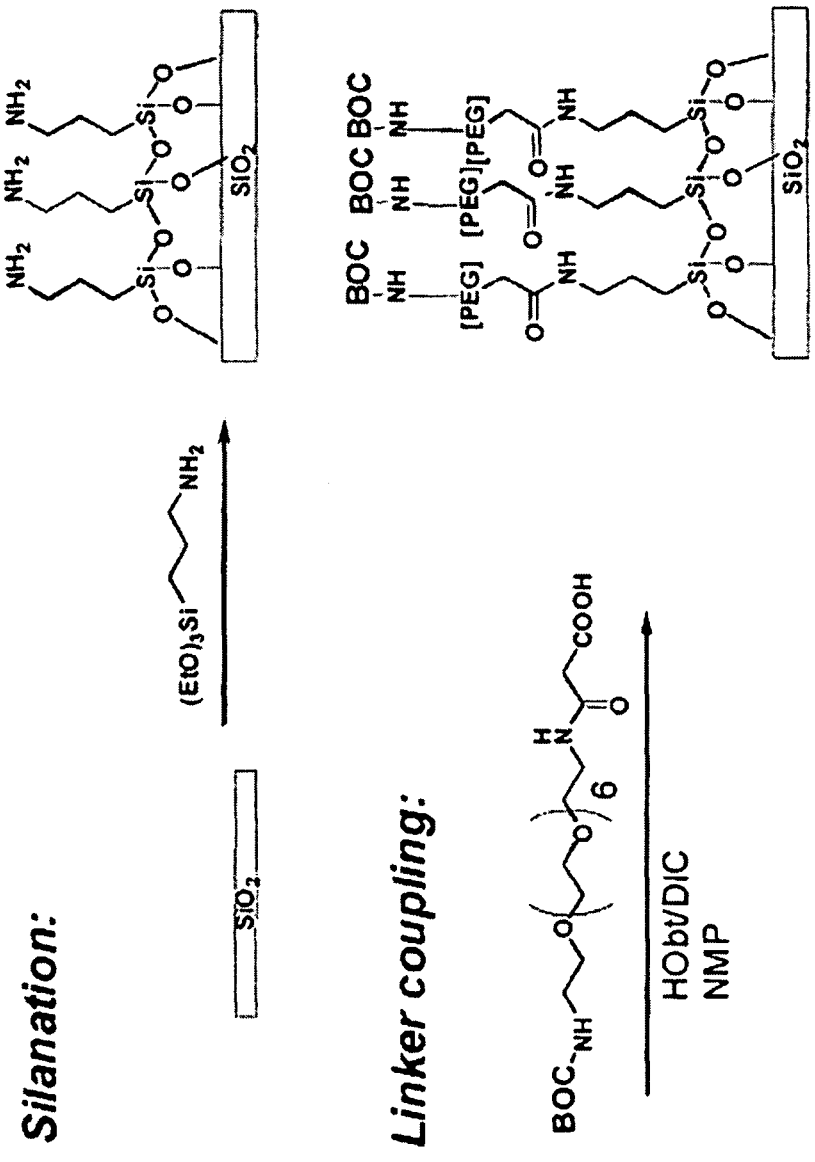
FIG. 3 shows a method for derivatizing a $SiO_2$ surface and attaching a linker molecule to the derivatized surface.

FIG. 3 provides a method for derivatization of a SiO$_2$ surface and linking of polymeric molecules to the surface. In FIG. 3 the SiO$_2$ surface is silanated by reacting it with aminopropyltriethoxy silane (APTES). The resulting surface presents an amine functional group for further reaction, such as peptide bond formation. Modulation of the density of polymers on the surface can be attained by silanation. For example, density can be modulated by mixing a functionalizable silane for example, APTES, with a non-functional silane (a silane with no non silyl functional group), for example, propyltrialkoxy silane. The derivatized surface can then be reacted with a linker. In this example, the linker is a polyethylene glycol molecule having an amine group protected with BOC at one terminus and a peptide-bond forming group at the second terminus. This coupling reaction can be accomplished in a solution of 1-hydroxybenzotriazole (HOBt) and diisopropylcarbodiimide (DIC) in N-methylpyrrolidone (NMP). The linker molecule serves to separate polymer (peptide) that is subsequently synthesized from surface of the substrate.

Figure 4:
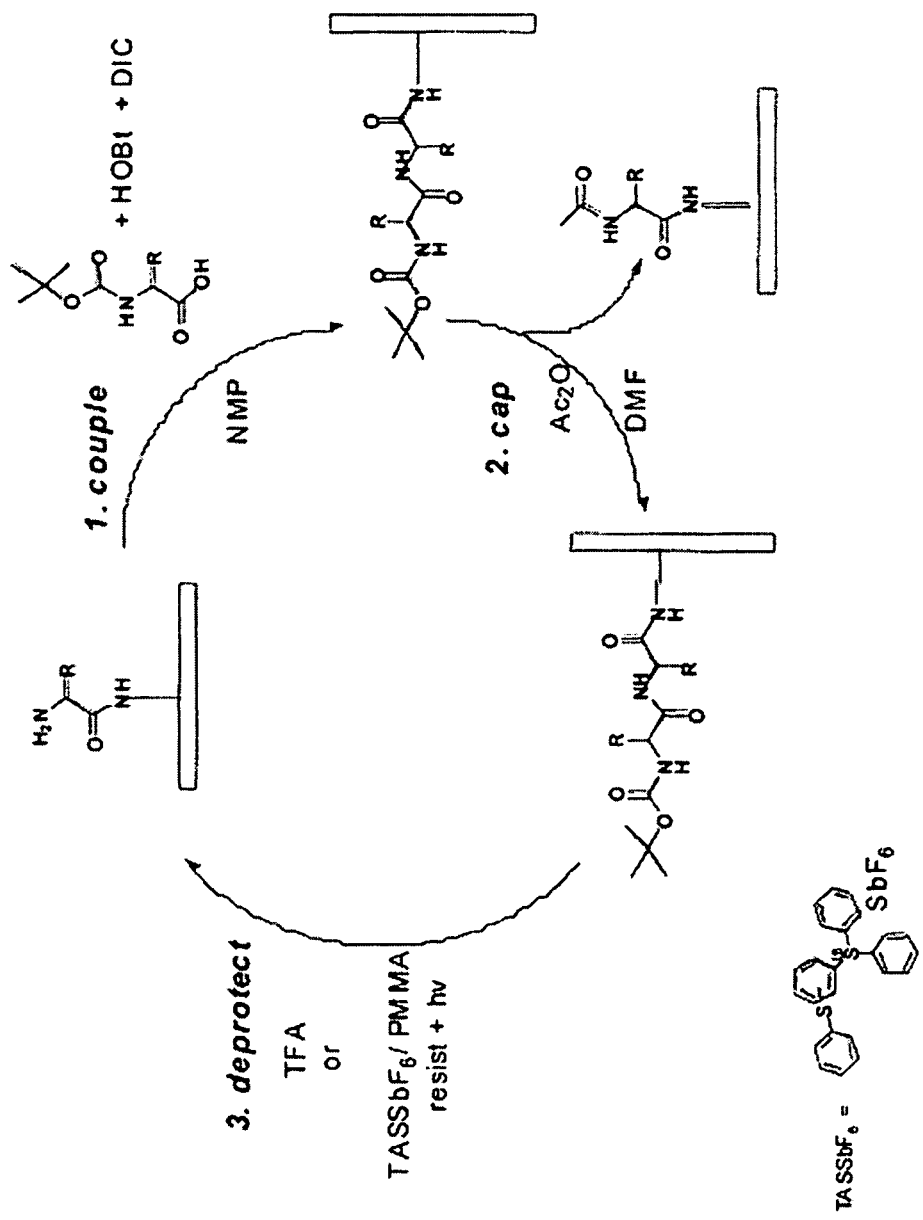
FIG. 4 demonstrates a method for solid phase peptide synthesis according to embodiments of the invention.

FIG. 4 shows a general scheme for solid-phase peptide synthesis. A substrate surface is provided having a first amino acid attached to the surface. A second amino acid having a protecting group is coupled to the first amino acid. In this example, the second amino acid is N-protected with a BOC protecting group. The coupling reaction is performed in a solution of 1-hydroxybenzotriazole (HOBt) and diisopropylcarbodiimide (DIC) in N-methylpyrrolidone (NMP). Unreacted amine groups are capped using an acetic anhydride (Ac$_2$O) solution in dimethylformamide (DMF). The substrate surface is then coated with a photoresist. In this example, the photoresist is comprised of PMMA polymer, TASSbF$_6$ (photoactivated acid generator), and PGMEA (as a solvent). (In FIG. 4, TFA represents trifluoroacetic acid, the acidic cleaving reagent typically used for bulk solid-phase peptide synthesis. Experiments demonstrated that yields for a peptide synthesis process according to the current invention were similar to yields for bulk solid-phase synthesis procedures using TFA as a protecting group removal catalyst.) Upon exposure to radiation, in this case UV radiation, an acid is produced in the photoresist and the N-protecting group is removed from the attached peptide in the region of UV exposure. By repeating the process shown in FIG. 4, peptides of desired sequence and length is selected regions upon the substrate surface can be produced.

Figure 5:
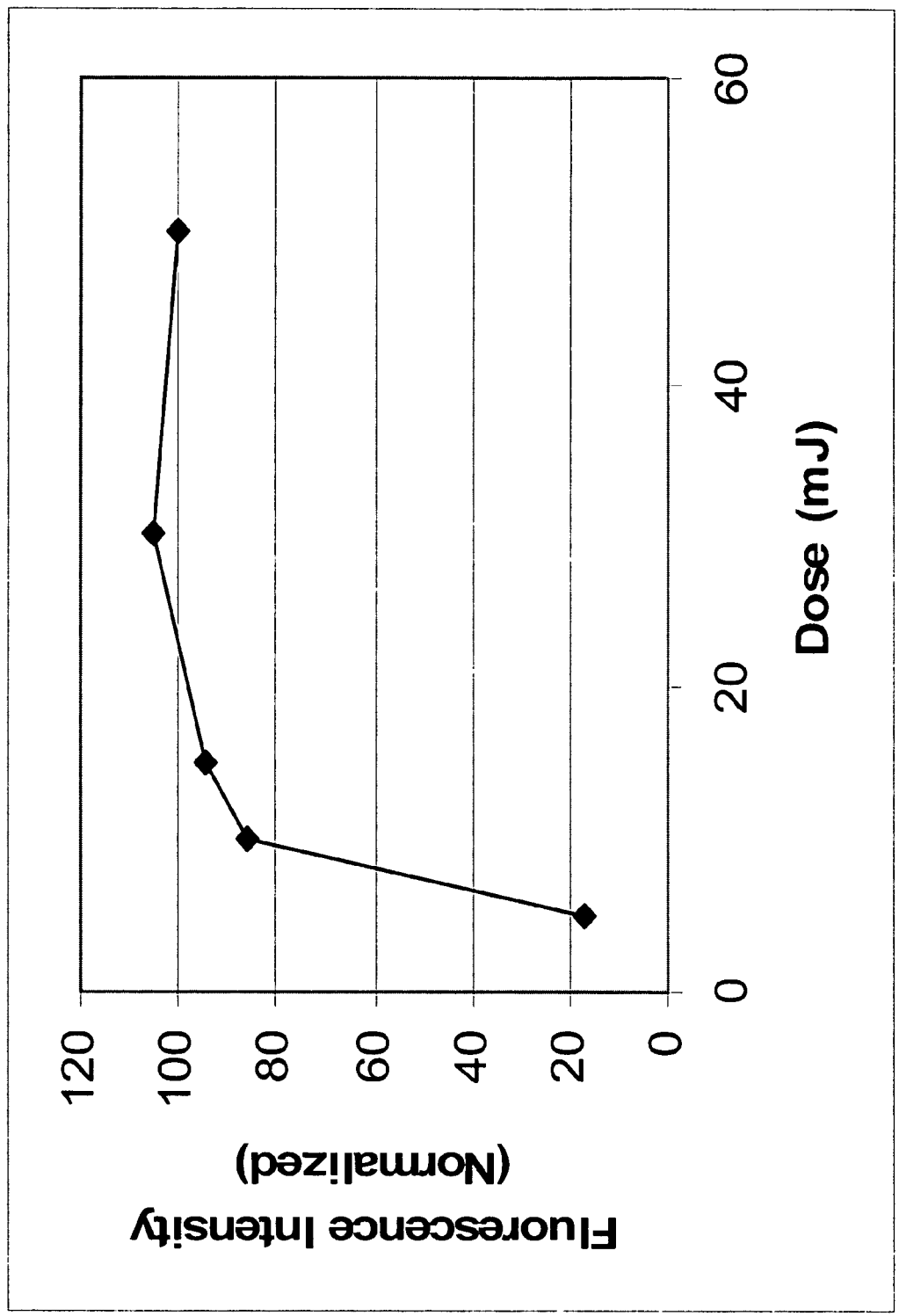
FIG. 5 graphs the photo-generated acid induced deprotection of glycine (as measured by fluorescence intensity) as a function of UV irradiation intensity.
Figure 6:
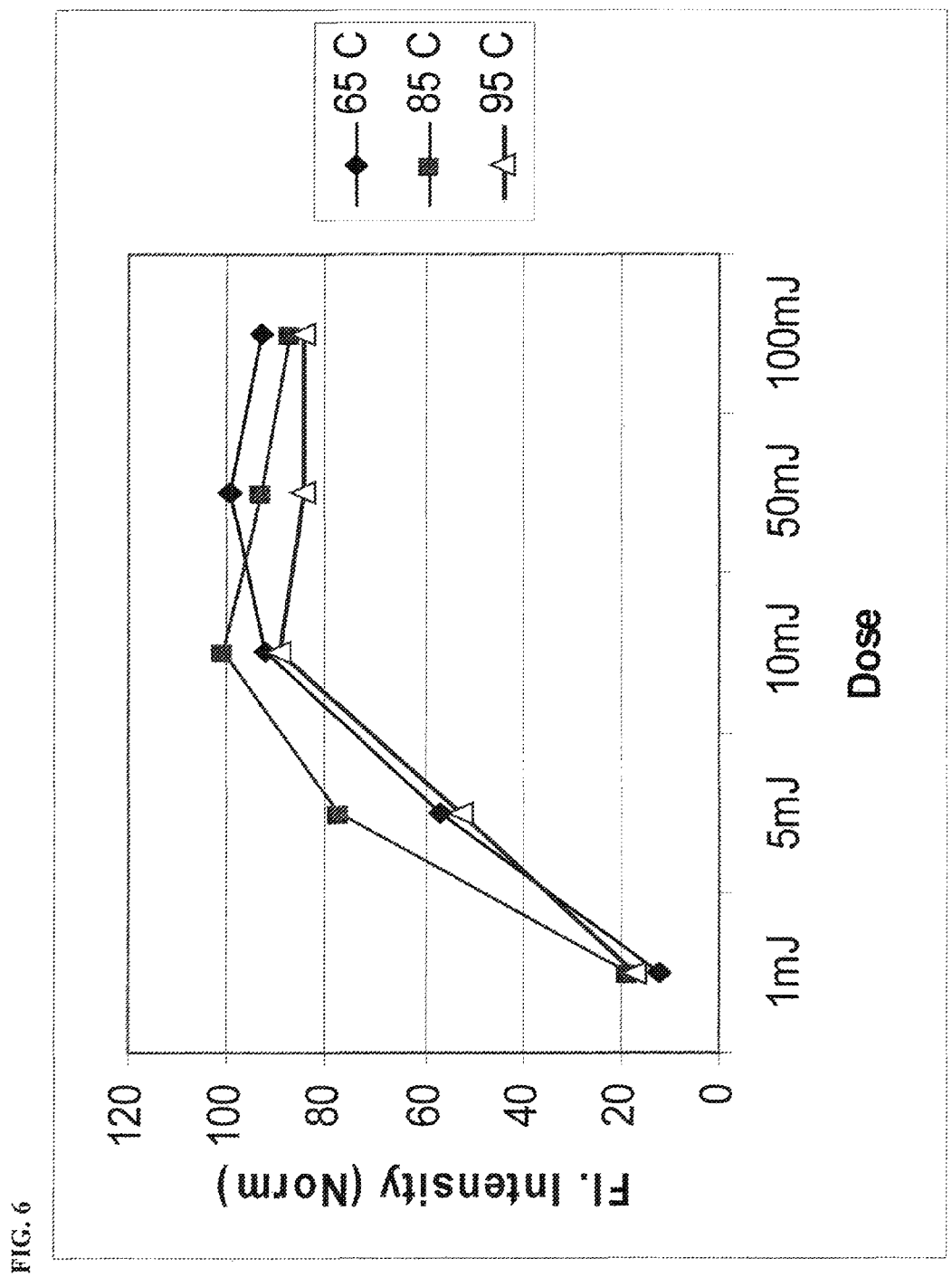
FIG. 6 demonstrates the post exposure bake temperature dependence of a photo-generated acid-induced deprotection reaction (deprotection of t-BOC-glycine) as measured by surface fluorescence of a fluorescent molecule coupled to the deprotected amino acid.
Figure 7:
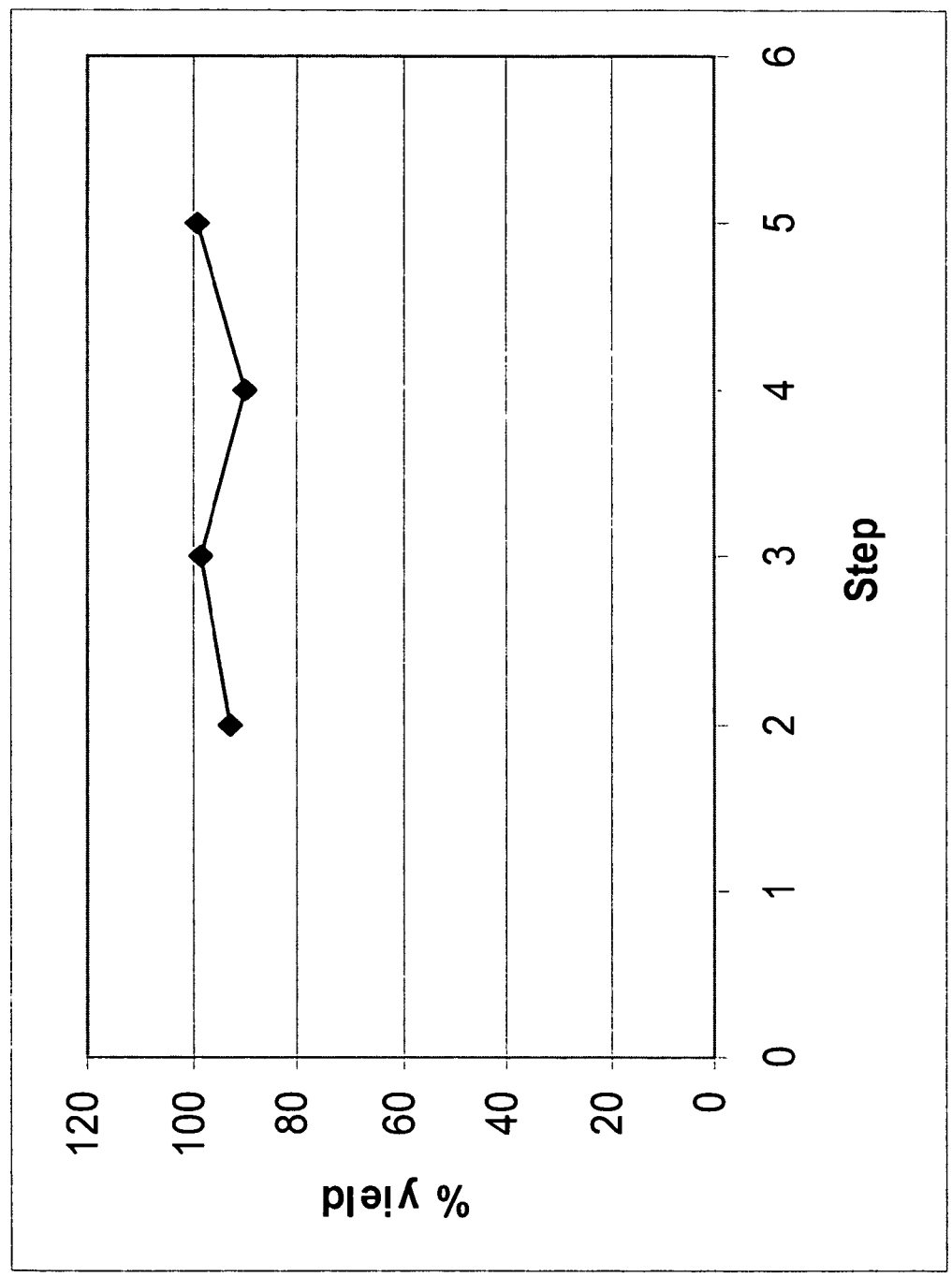
FIG. 7 graphs the stepwise synthesis efficiency for the synthesis of a penta glycine peptide.

In a further embodiment, a photoactive layer (photoresist) formulation for high throughput solid phase synthesis of peptide microarrays that requires very low energy for photo acid generation and deprotection of a t-BOC protecting group is provided. The formulation includes poly methyl methacrylate (PMMA) polymer, Bis(4-tert-butylphenyl)iodonium triflate (photo generated acid, PAG) and sensitizer, isopropylthioxanthenone (ITX) in propylene glycol methyl ether acetate (PGMEA). The energy requirement for deprotection of amino acids is as low as 10-50 mJ as shown in FIG. 5. In FIG. 5, the fluorescence intensity obtained from PAG deprotected amines (t-BOC-glycine) that were coupled to carboxyfluorescein was normalized to the fluorescence intensity obtained from amines that were deprotected by trifluoroacetic acid (TFA) and coupled to carboxyfluoroescein, and was plotted as a function of exposure dose. Referring to FIG. 6, the energy dose requirement was sensitive to the post exposure bake temperature, so that increasing the post exposure bake temperature from 65° C. to 85° C. reduced the required exposure dose, but a further increase to 95° C. did not reduce the required exposure dose. The energy requirement for deprotection of amino acids is as low as 10-50 mJ as shown in FIG. 6. Referring to FIG. 7, the step wise yield (efficiency) for synthesizing a penta glycine peptide using the photoactive layer formulation was found to be consistent at 92-98% in each step.

Deprotection and amino acid coupling efficiencies are determined by Fluorescein staining. Briefly, surfaces with Boc protected amino groups are treated with either TFA (control) or photogenerated acid. Carboxyfluorescein/Boc-Gly-OH (1:9 molar ratio, to avoid quenching) is then couple to the free amino groups and their fluorescence intensities are then measured on a confocal microscope. Boc deprotection efficiency with PGA is then calculated from the ratio of the fluorescence intensities of IPGA/ITFA. To determine stepwise yield, fluorescence staining is performed after attachment of every amino acid. Relative yield for each synthesis cycle is then calculated from the ratio of adjacent amino acids, that is: % coupling efficiency of second amino acid AA2= (IAA2/IAA1)×100.

The details of the Fluorescein staining technique are shown below in Table 2.

TABLE 2

Fluorescein staining procedure
Fl-AA coupling soln 0.1 M (FL/Gly/DIC)

| REAGENTS | Source | MW (g/mol) | d (g/ml) | molar ratio | final conc (M) | final vol (L) | moles | grams | mls |
|---|---|---|---|---|---|---|---|---|---|
| Carboxy-fluorescein | Aldrich | 376.32 | | 0.1 | 0.01 | 0.001 | 0.00001 | 0.0038 | |
| Boc-Gly-OH | Nova | 175.19 | | 0.9 | 0.09 | 0.001 | 0.00009 | 0.0158 | |
| HOBt | Aldrich | 135.13 | | 1 | 0.1 | 0.001 | 0.0001 | 0.0135 | |
| DIC | Aldrich | 126.2 | 0.815 | 1 | 0.1 | 0.001 | 0.0001 | 0.0126 | 0.0155 |
| NMP | Fluka | | | | | 0.001 | | | |

Remove Boc by treating slides with TFA for 15 min
Wash with IPA 3x
Wash with DMF for 5 min
Dip slide into 5% (v/v) DIEA/DMF for 5 min
Wash 2x with DMF, 2x with NMP and rinse with IPA
Place PMA gel with pierced circles on one side of the slide
Add 30 ul of coupling solution in each well, cover with aluminum foil to protect from light
Let it sit for two hours
Remove solution from wells and wash 2x with NMP
Remove PMA gel and rinse slide with NMP, IPA and ethanol
Dip slide into 50% EDA/EtOH for 30 min
Wash 2x with EtOH, 15 min ea
Rinse with IPA and dry with N2
Lay down the slide and add 1 drop of TE buffer, pH 8 and cover with cover slip
Scan fluorescence on confocal microscope at 494 nm/525 nm (Ex/Em)

In general, methods according to the disclosed invention are useful for the synthesis of polymers on a substrate. Highly parallel synthesis of varied polymers can be accomplished through matching the radiation-activated deprotection catalyst to the protection scheme chosen for the monomers.

EXAMPLES

Photolithography is a complex process with many variables contributing to its process latitude, such as reduced feature size, alignment tolerance, number of masking layers, and cleanliness of the wafer surface. The patterning process of photolithography could be divided into an eight-step procedure as follows: (1) prime; (2) spin coat; (2) soft bake; (4) alignment and exposure; (5) post-exposure bake (PEB); (6) develop and rinse; (7) hard bake; and (8) development inspection. In wafer fabrication, these steps are often referred to as operations or modules.

By the embodiments of the invention, the photolithography process can be modified and integrated high volume manufacturing of micro arrays. Automated equipment, referred to as a coater/developer track system, or tracks, could employ robots, automated material handling, and computers to perform all eight steps without human intervention. Integrated tracks could offer many benefits over the previous stand-alone manual tooling for photolithography: controlling delays between process steps, processing wafers efficiently, increasing flexibility, reducing contamination due to environmental control and minimal operator handling, and increasing safety due to reduced operator exposure to chemicals.

Details of the synthesis cell are shown in Table 3.

TABLE 3

Details of the Synthesis Cell

| Step | Description | Chemical | Time |
|---|---|---|---|
| 1 | Wafer substrate preparation | | |
| 1.1 | cleaning | 1:1 $H_2SO_4$ & $H_2O_2$ at room temp. | 30 min. |
| 1.2 | coating with $NH_2$ linker | Washing with deionized water and 95% ethanol and dry in $N_2$ 3-aminopropyltriethoxysilane (0.5%) in 190 proof ethanol | 30 min. |
| 1.3 | curing | Wash with ethanol & dried in $N_2$ cured under $N_2$ at 110° C. | 1 hr. |
| 2 | Coupling first amino acid | | |
| 2.1 | Activation + Coupling | 0.1M solution of Boc-aa, DIC, HoBt in NMP for 1 h at RT | 0.5-1 h |
| 2.2 | Wash | Wash with NMP and DMF in that order | |
| 3 | Capping | 5% acetic anhydride in DMF | 30 min |
| | Wash | DMF wash followed by IPA rinse and $N_2$ drying | 5 min |

TABLE 3-continued

Details of the Synthesis Cell

| Step | Description | Chemical | Time |
|---|---|---|---|
| 4 | BOC Deprotection | | |
| 4.1 | Photo resist | Photoresist formulation: 2.5% PMMA (24K), 5% PAG (Bis(4-tert-butylphenyl)iodonium triflate), 5% ITX (isopropylthioxanthenone) sensitizer in PGMEA | |
| 4.2 | Spin | Spin 2000 RPM for 60 s | 60 s |
| 4.3 | Soft Bake | 85 C. for 90 s | 90 s |
| 4.4 | Litho exposure | Exposure dose 50 mJ at 365 nm | 5 secs. |
| 4.5 | Post exposure Bake | Bake at 65 C. for 60 s. | |
| 4.6 | Strip | Stripping by Acetone rinse at 2000 rpm for 30 sec followed by isopropanol rinse | 1-2 min |
| 4.7 | Dry | Spin dry or blow dry with $N_2$ | |
| 5 | Neutralization | 5% diisopropylethylamine (DIEA) in DMF | 5 min |

In Tables 1 and 2, Boc-aa is t-butoxy carbonyl protected amino acid and IPA is isopropyl alcohol. Other abbreviated terms in these tables are defined therein or elsewhere in the specification.

Example 1

Referring to FIG. 1G, a glass substrate was silanated using a solution of 3% APTES (aminopropyl triethoxy silane) in 95% ethanol. The surface of the substrate was then washed and annealed at about 100° C. for about 1 hour. The substrate was then treated with a 1:1 solution of DIEA (diisopropyl ethyl amine) in DMF (dimethylformamide). A spacer molecule was then coupled to the surface using a solution of 0.25 M solution of O—(N-Boc-2-aminoethyl)-O'—(N-diglycolyl-2-aminoethyl)hexaethyleneglycol, 0.25 M HOBt, and 0.25 M DIC (diisopropylcarbodiimide) in NMP (N-methylpyrrolidone) and gentle agitation over the surface of the substrate in a sealed container for about 30 min. The solution was then discarded and the surface replenished with fresh solution. After coupling was complete, the surface was washed with NMP and then acetone. Unreacted surface amine groups were capped by treatment with 1:1 acetic anhydride in DMF solution (a 50% acetic anhydride solution in DMF) for about 30 minutes. The surface was then washed.

A photoresist was prepared by mixing about 10% by mass of PMMA, 20% by mass of triarylsulfonium hexafluoroantimonate in PGMEA solvent and spin coating the mixture over the amino acid derivatized glass surface for about 60 seconds at 2,000 rpm. The photoresist may also optionally contain thioxanthenone, a photosensitizer. The photoresist layer was baked at about 85° C. for about 90 seconds. The resulting photoresist layer had a thickness of about 2 μm.

Acid was generated in the photoresist layer by irradiation of the surface of the substrate with 2-3 J of 365 nm UV light through a mask. The reaction was accelerated by a post exposure bake at about 65° C. for about 60 seconds. After the photogenerated acid deprotection was achieved, the surface of the substrate was rinsed with acetone to strip the photoresist from the surface and the surface was dried. The surface was neutralized by treatment in 25% DIEA/DMF for about 5-10 minutes and then washed in DMF.

A second amino acid (Boc-Leu-OH) was coupled to the surface of the substrate using a 0.25 M solution of N-a-Boc-Leu, HOBt, and DIC as above. Subsequent rounds of coupling and deprotection were accomplished by repeating the above procedures to generate peptides of a desired length. As a result, a hexamer peptide, SDLYKL (SEQ ID NO: 1) segment of human tumor suppressor protein p53, was synthesized on an APTES surface derivatized with a PEG (polyethylene glycol) spacer. A labeled Fl-tagged anti-p53 monoclonal antibody in a standard Ab binding assay recognized and strongly bound to the SDLYLK (SEQ ID NO: 1) peptide on the surface as determined by fluorescence detection.

Example 2

An array of wildtype (SDLHKL) (SEQ ID NO: 2) and mutant (AGLHKL) (SEQ ID NO: 3) peptide was synthesized on an aminated glass surface with a linker molecule, O—(N-Boc-2-aminoethyl)-O'—(N-diglycolyl-2-aminoethyl) hexaethyleneglycol, for spacing the peptides from the surface. The peptides were synthesized in a checkerboard pattern using uniform photodeprotection of t-Boc protecting groups through an open grid mask till the second leucine and spatially localized deprotection through a checkerboard mask for the last two amino acid couplings.

The photodeprotection and coupling of linker molecules and amino acids was carried out as described in Example 1.

The peptide array was incubated for 1 hour with 5 μg/ml monoclonal antibody known to specifically recognize the SDLHKL (SEQ ID NO: 2) epitope of human p53 protein. A second incubation was performed with fluorescein-labeled rabbit antibody raised against mouse antibody at a 1:100 dilution in phosphate buffered saline with 0.05% Tween 20. A fluorescent checker board pattern was detected on fluorescence scanning of the array suggesting specific interaction of antibody with the wildtype sequence.

Example 3

Photoresist formulations may include a sensitizer in addition to the photogenerated acid catalyst to generate the acid deprotection catalysts. In general, the amount of PMMA in the resist in these exemplary formulations may vary between about 3% and about 50%.

Useful photoresists may be made using diaryliodonium salts (DAI) and photosensitizers. The mass ration between DAI and photosensitizer may be between about 1:10 and 1:1. For instance, (tolylcumyl)polonium tetrakis(pentafluorophenyl) borate with isopropyl-9H-thioxanthen-9-one may be formulated in a 1:10 or 1:1 (or a ratio there between) in PMMA and PGMEA to form final concentrations of between about 0.5% to 10% by mass DAI. The formulation selected may be spun coated on the substrate surface and baked. The radiation exposure dose may be between about 0.02 J and about 10 J. Post exposure baking may be conducted for about 30 to 60 seconds at about 40° C. to about 85° C.

Example 4

A glass substrate was cleaned in a 1:1 $H_2O_2/H_2SO_4$ solution for 1 hour, washed in deionized water and 95% ethanol. The surface was then functionalized with 0.5% aminopropyl triethoxy silane (APTES) in ethanol for 30 minutes, washed with ethanol and subsequently cured at 110° C. for 1 hour. T-BOC protected glycine was coupled to the amino functionalized surface at 0.1 M concentration in a solution containing 0.1 M DIC and HOBt (diisopropyl carbodiimide and hydroxybenzotriazole, activators) in N-methyl-2-pyrrolidinone (NMP) for 30 min. The unreacted amino groups of the surface were capped using a 50% acetic anhydride solution in dimethylformamide (DMF) for 30 min.

The photosensitive resist was prepared by mixing 2.5 PMMA, 5% PAG, and 5% ITX sensitizer in PGMEA. The photosensitive layer was deposited by spin coating at 2000 rpm for 60 sec in a spin coater. The film was subsequently baked at 85° C. for 90 sec. A 0.3 μm thick photosensitive film was thus formed. The substrate with photosensitive layer was then exposed to UV radiation at 365 nm at 1 mJ to 100 mJ dose to generate acid followed by post exposure at 65° C. to 85° C. for 1 min to accelerate deprotection of t-BOC group. The deprotection was monitored by coupling 5,6-carboxyfluorescein (1:9 fluorescein:t-BOC-Gly-OH in 0.1 M solutions) to the terminal free amines and assessing intensity by fluorescence scanning.

Figure 8:
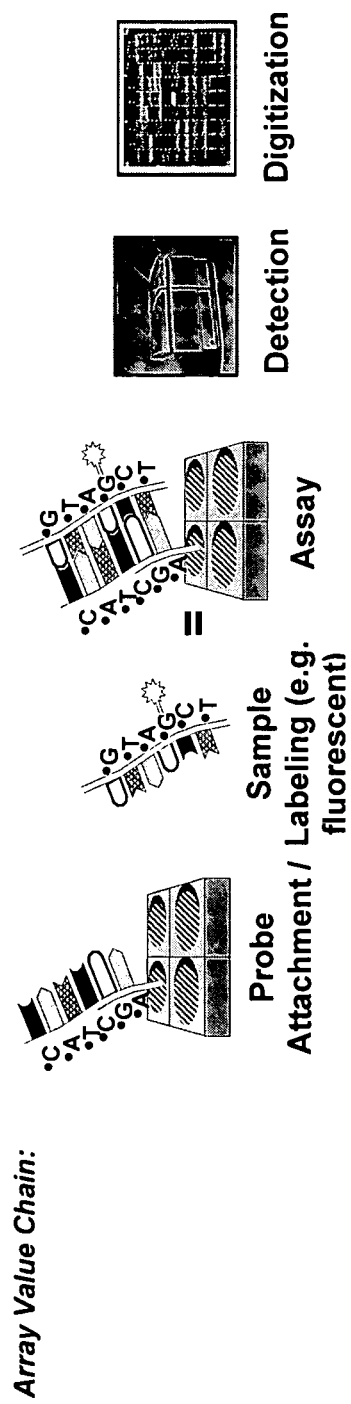
FIG. 8 schematically illustrates a method of detection of an analyte with a fluorescent-type tag using a conventional microarray.

In the embodiments of the invention, the detection of chemical reaction or binding on a microarray could be accomplished, for example, with a multi-step process as shown in FIG. 8. For example, the analyte in the sample could be labeled with a fluorescent or other tag (e.g. luminescent, radioactive, dye, etc.). A sample could be washed over the array and analytes bind to their complementary probes on the surface due to hybridization. When binding occurs to the probe on the substrate, the label would be bound to a location on the substrate. An instrument could be used to illuminate the tag creating a spot visible to a reader. Often, fluorescent labels are used and read with an instrument employing laser illumination and a CCD camera to digitize the location and brightness of bound labels.

Example 5

A layer of t-butoxycarbonyl N-protected leucine was coupled to an amino functionalized glass substrate. The amino acid was attached to the glass surface in 250 mM equimolar solution of amino acid, diisopropylcarbodiimide (DIC) and 1-hydroxybenzotriazole (HOBt) in dimethylformamide (DMF). Any unreacted reactive amino groups were capped by reacting them with a solution of 50% acetic anhydride in DMF.

A photoresist was prepared by mixing about 10% by mass of PMMA, 20% by mass of triarylsulfonium hexafluoroantimonate in PGMEA solvent and spin coating the mixture over the amino acid derivatized glass surface for about 60 seconds at 2,000 rpm. The photoresist may also optionally contain thioxanthenone, a photosensitizer. The photoresist layer was baked at about 85° C. for about 90 seconds. The resulting photoresist layer had a thickness of about 2 μm.

The glass substrate having the photoresist layer was then exposed to 365 nm UV radiation for about 3.5 minutes. The photoresist layer was then baked at about 65° C. for about 60 seconds to accelerate the cleavage of the t-butoxycarbonyl group by the photogenerated acid.

A second amino acid, Boc-Lys(Z)—OH was then coupled to the de-protected leucine layer at 250 mM concentration. The reaction was allowed to proceed for about 1 hour. Tyrosine, leucine, aspartic acid, and serine were subsequently coupled in that order to yield a peptide corresponding to the N-terminal sequence of human p53 protein, residues 20-25 (SDLYKL, ser-asp-leu-tyr-lys-leu, SEQ ID NO: 1).

The peptide sequence attached to the glass surface was detected using fluorescently tagged antibody specific for the N-terminal sequence of the human p53 protein.

This application discloses several numerical range limitations that support any range within the disclosed numerical ranges even though a precise range limitation is not stated verbatim in the specification because the embodiments of the invention could be practiced throughout the disclosed numerical ranges. Further, the entire disclosure of the patents and publications referred in this application, if any, are hereby incorporated herein in entirety by reference.

The invention claimed is:

1. An apparatus configured to make a biomolecule microarray without human intervention, the apparatus comprising a track system, the track system being configured for inline processing and comprising a spacer attachment module adapted to attach a linker to a substrate surface of the biomolecule microarray, a coupling module adapted to couple a molecule to the linker, the molecule being a nucleotide or an amino acid and respectively being capable of forming an amide bond or a phosphodiester bond when the molecule is not bound to a protecting group that respectively prevents the formation of the amide or phosphodiester bond, the molecule being bound to the protecting group, and a deprotection module adapted to create deprotection of the protecting group with a radiation exposure of about 1-50 mJ/cm$^2$;
wherein the deprotection of the protecting group is by generating photo acid in a photoresist comprising poly methyl methacrylate, Bis(4-tert-butylphenyl)iodonium triflate and isopropylthioxanthenone in propylene glycol methyl ether acetate.

2. The apparatus of claim 1, wherein the spacer attachment module comprises a developer module and a hot plate module adapted to cure the linker on the substrate surface.

3. The apparatus of claim 2, wherein the developer module is adapted with a puddle mechanism and a spin-wash mechanism.

4. The apparatus of claim 2, wherein the spacer attachment module further comprises a chill plate module.

5. The apparatus of claim 1, wherein the spacer attachment module comprises a vapor prime module and a hot plate module adapted to cure the linker on the substrate surface.

6. The apparatus of claim 5, wherein the vapor prime module is a hexamethyldisilazane (HMDS) vapor prime module.

7. The apparatus of claim 5, wherein the spacer attachment module further comprises a chill plate module.

8. The apparatus of claim 1, wherein the coupling module comprises a developer module.

9. The apparatus of claim 8, wherein the developer module is adapted with a puddle mechanism and a spin-wash mechanism.

10. The apparatus of claim 8, wherein the developer module is adapted with a mechanism to cap an unreacted linker on the substrate surface.

11. The apparatus of claim 1, wherein the deprotection module comprises a spin coater module adapted to deposit a photoactive layer on the substrate surface.

12. The apparatus of claim 11, wherein the deprotection module further comprises a hot plate module adapted to bake the photoactive layer.

13. The apparatus of claim 12, wherein the deprotection module further comprises a chill plate module adapted to cool the photoactive layer.

14. The apparatus of claim 1, wherein the deprotection module comprises an alignment and exposure module adapted to remove the protecting group.

15. The apparatus of claim 14, wherein the alignment and exposure module adapted to remove the protecting group with the radiation exposure of about 10-50 mJ/cm$^2$.

16. The apparatus of claim 15, wherein the radiation exposure is an ultraviolet radiation exposure.

17. The apparatus of claim 14, wherein the alignment and exposure module comprises a stepper platform.

18. The apparatus of claim 17, wherein the stepper platform is adapted to step and scan with ability to handle one or more reticles.

19. The apparatus of claim 17, wherein the stepper platform is adapted to perform maskless lithography.

20. The apparatus of claim 14, wherein the deprotection module further comprises a developer module adapted to strip a photoactive layer on the substrate surface.

21. The apparatus of claim 1, wherein the track system is enclosed inside an enclosure, air in the enclosure being filtered using a filter that filters ozone.

22. The apparatus of claim 1, wherein the photoresist comprises 2.5% poly methyl methacrylate, 5% Bis(4-tert-butylphenyl)iodonium triflate, and 5% isopropylthioxanthenone.

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: N-terminal residues 20-25 of human tumor
      suppressor protein p53

<400> SEQUENCE: 1

Ser Asp Leu Tyr Lys Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Segment of wildtype human tumor suppressor
      protein p53
```

```
<400> SEQUENCE: 2

Ser Asp Leu His Lys Leu
1               5

<210> SEQ ID NO 3
<211> LENGTH: 6
<212> TYPE: PRT
<213> ORGANISM: Artificial Sequence
<220> FEATURE:
<223> OTHER INFORMATION: Segment of mutant human tumor suppressor
      protein p53

<400> SEQUENCE: 3

Ala Gly Leu His Lys Leu
1               5
```